US007166299B2

(12) United States Patent
Yoo

(10) Patent No.: US 7,166,299 B2
(45) Date of Patent: Jan. 23, 2007

(54) PREPARATION OF AQUEOUS CLEAR SOLUTION DOSAGE FORMS WITH BILE ACIDS

(76) Inventor: Seo Hong Yoo, 537 Spencer Dr., Wyckoff, NJ (US) 07481

( * ) Notice: Subject to any disclaimer, the term of this patent is extended or adjusted under 35 U.S.C. 154(b) by 218 days.

(21) Appl. No.: 10/309,603

(22) Filed: Dec. 4, 2002

(65) Prior Publication Data
US 2003/0186933 A1      Oct. 2, 2003

Related U.S. Application Data

(60) Division of application No. 09/778,154, filed on Feb. 5, 2001, and a continuation-in-part of application No. 09/357,549, filed on Jul. 20, 1999, now Pat. No. 6,251,428.

(60) Provisional application No. 60/180,268, filed on Feb. 4, 2000, provisional application No. 60/094,069, filed on Jul. 24, 1998.

(51) Int. Cl.
*A61K 9/66* (2006.01)
(52) U.S. Cl. .............. 424/455; 424/456; 424/424; 424/479
(58) Field of Classification Search ........... 424/455, 424/456, 479
See application file for complete search history.

(56) References Cited

U.S. PATENT DOCUMENTS

| 3,845,770 | A |   | 11/1974 | Theeuwes et al. ........ 128/260 |
|---|---|---|---|---|
| 3,916,899 | A |   | 11/1975 | Theeuwes et al. ........ 128/260 |
| 4,320,146 | A |   | 3/1982 | Walser ..................... 424/319 |
| 4,327,725 | A |   | 5/1982 | Cortese et al. ............. 128/260 |
| 4,585,790 | A |   | 4/1986 | Padfield et al. ............ 514/471 |
| 4,681,876 | A |   | 7/1987 | Marples et al. ............ 514/182 |
| 5,057,321 | A |   | 10/1991 | Edgren et al. ............. 424/413 |
| 5,149,537 | A |   | 9/1992 | Azria et al. ............... 424/436 |
| 5,157,022 | A |   | 10/1992 | Barbul ..................... 514/18 |
| 5,260,074 | A |   | 11/1993 | Sipos ....................... 424/497 |
| 5,269,011 | A | * | 12/1993 | Yanai et al. ............... 710/100 |
| 5,300,300 | A |   | 4/1994 | Egidio et al. .............. 424/456 |
| 5,302,398 | A |   | 4/1994 | Egidio et al. .............. 424/474 |
| 5,302,400 | A |   | 4/1994 | Sipos ....................... 424/494 |
| 5,310,560 | A |   | 5/1994 | Widauer .................... 424/451 |
| 5,324,514 | A |   | 6/1994 | Sipos ....................... 424/94.63 |
| 5,380,533 | A |   | 1/1995 | Egidio et al. .............. 424/456 |
| 5,446,026 | A |   | 8/1995 | Ruff et al. ................. 514/15 |
| 5,470,581 | A |   | 11/1995 | Grillo et al. ............... 424/479 |
| 5,484,776 | A |   | 1/1996 | Racz et al. ................ 514/54 |
| 5,534,505 | A |   | 7/1996 | Widauer .................... 514/169 |
| 5,578,304 | A |   | 11/1996 | Sipos ....................... 424/94.1 |
| 5,641,767 | A |   | 6/1997 | Wess et al. |
| 5,653,987 | A |   | 8/1997 | Modi et al. ................ 424/400 |
| 5,686,588 | A |   | 11/1997 | Yoo |
| 5,843,929 | A |   | 12/1998 | Larson et al. .............. 514/182 |
| 5,846,964 | A |   | 12/1998 | Ozeki ....................... 514/182 |
| 5,858,998 | A |   | 1/1999 | Leuschner ................. 514/171 |
| 5,863,550 | A |   | 1/1999 | Maeda et al. .............. 424/423 |
| 5,942,248 | A | * | 8/1999 | Barnwell ................... 424/457 |
| 5,945,411 | A |   | 8/1999 | Larson et al. .............. 514/171 |
| 5,977,070 | A | * | 11/1999 | Piazza et al. ............... 514/12 |
| 6,251,428 | B1 | * | 6/2001 | Yoo ........................ 424/455 |

FOREIGN PATENT DOCUMENTS

| EP | 0312052 A1 |   | 4/1989 |
|---|---|---|---|
| JP | 55022616 A |   | 2/1980 |
| JP | 62153220 | * | 7/1987 |
| JP | 62153220 A |   | 7/1987 |

OTHER PUBLICATIONS

Graham et al., "*H. pylori* in the Pathogenesis of Durodenal Ulcer: Interaction Between Duodenal Acid Load, Bile, and *H. pylori*", American Journal of Gastroenterology (2000), vol. 95, No. 1, pp. 87-91.
Hammad et al., "Solubility and Stability of Lorazepam in Bile Salt/Soya Phosphatidylcholine-Mixed Micelles", Drug Development and Industrial Pharmacy. (1999) vol. 25, No. 4, pp. 409-417.
Itoh et al. "The interaction of bile acids and *Helicobacter pylori*", J. GASTROENTEROL (1999), 34:653-654.
Invernizzi et al., "Differences in the Metabolism and Disposition of Ursodeoxycholic Acid and of its Taurine-Conjugated Species in Patients with Primary Biliary Cirrhosis", HEPATOLOGY, (1999) vol. 29, No. 2 pp. 320-327.
Itoh et al., "Antibacterial action of bile acids against *Helicobacter pylori* and changes in its ultrastructural morphology: effect of unconjugated dihydroxy bile acide", J. GASTROENTEROL, (1999) 34:571-576.
Knopp et al., "Long-Term Blood Cholesterol-Lowering Effects of a Dietary Fiber Supplement", Am J Pre. Med (1999) 17(1):18-23.
F. Lanzarotto et al., "Effect of Long-Term Simvastatin Administration as an Adjunct to Ursodeoxycholic Acid: Evidence for a Synergistic Effect on Biliary Bile Acid Composition but Not on Serum Lipids in Humans", GUT, (1999) vol. 4 pp. 552-556.

(Continued)

*Primary Examiner*—Vickie Kim
(74) *Attorney, Agent, or Firm*—Baker Botts L.L.P.

(57) ABSTRACT

Compositions for pharmaceutical and other uses comprising clear aqueous solutions of bile acids which do not form any detectable precipitates over selected ranges of pH values of the aqueous solution and methods of making such solutions. The compositions of the invention comprise water; a bile acid in the form of a bile acid, bile acid salt, or a bile acid conjugated with an amine by an amide linkage; and either or both an aqueous soluble starch conversion product and an aqueous soluble non-starch polysaccharide. The composition remains in solution without forming a precipitate over a range of pH values and, according to one embodiment, remains in solution for all pH values obtainable in an aqueous system. The composition, according to some embodiments, may further contain a pharmaceutical compound in a pharmaceutically effective amount. Non-limiting examples of pharmaceutical compounds include insulin, heparin, bismuth compounds, amantadine and rimantadine.

24 Claims, 12 Drawing Sheets

OTHER PUBLICATIONS

Leuschner et al., "Oral Budesonide and Ursodeoxycholic Acid for Treatment of Primary Biliary Cirrhosis: Results of a Prospective Double-Blind Trial", GASTROENTEROLOGY, (1999) vol. 117 pp. 918-925.

Na et al., "Cloud Point of Nonionic Surfactants: Modulation with Pharmaceutical Excipients", Pharmaceutical Research, (1999) vol. 16, No. 4 pp. 562-568.

Osato et al., "Osmotic Effect of Honey on Growth and Viability of *Helicobacter pylori*", Digestive Diseases and Sciences, (1999) vol. 44, No. 3 pp. 462-464.

Sinisalo et al., "Ursodeoxycholic Acid and Endothelial-Dependent, Nitric Oxide-Independent Vasodilatation of Forearm Resistance Arteries in Patients with Coronary Heart Disease", Br. J. Clin. Pharamcol., (1999) vol. 47 pp. 661-665.

Verrips et al., "Effect of Simvastatin in Addition to Chenodeoxycholic Acid in Patients with Cerebrotendinous Xanthomatosis", METABOLISM, (1999) vol. 48, No. 2 pp. 233-238.

Wacker Biochem. Corp.. advertisement, *C&EN*, 31 (Apr. 12, 1999).

M. A. Hammad, B. W. Müller, Increasing Drug Solubility by Means of Bile Salt-Phosphatidylcholine-Based Mixed Micelles, European J. of Pharmaceutics and Biopharmaceutics. (1998) vol. 46 pp. 361-367.

M. A. Hammad et al., "Solubility and Stability of Tetrazepam in Mixed Micelles", European J. of Pharmaceutical Sciences, (1998) vol. 7 pp. 49-55.

Oliva et al., "Ursodeoxycholate Alleviates Alcoholic Fatty Liver Damage in Rats", Alcohol Clin Exp Res., (1998), vol. 22, No. 7,pp. 1538-1543.

Rodrigues et a;l, "Ursodeoxycholic Acid May Inhibit Deoxyxholic Acid-Induced Apoptosis by Modulating Mitochondrial Transmembrane Potential and Reactive Oxygen Species Production", Molecular Medicine (1998) 4: 165-178.

Invernizzi et al., "Ursodeoxycholate inhibits induction of NOS in human intestinal epithelial cells and in vivo", Am J Physiol (1997) 273:G131-138.

Shinya Nagamatsu, "Phase I Clinical Study of Ursodesoxycholic Acid", Jpn. Pharmacol. Ther., (1997) vol. 25, No. 6 pp. 145-159.

Keith D. Lindor, M.D., "Ursodiol For Primary Sclerosing Cholangitis", The New England Journal of Medicine, (1997) vol. 336, No. 10., pp. 691-695.

Binek et al., "Bedeutung von Ursodeoxycholsäure bei der Eradikation von *Helicobacter pylori*", Schweitz Med Wochenschr (1996) 126 (Suppl. 79): 44S-46S.

Crosignani, et al., "Clinical Pharamcokinetics of Therapeutic Bile Acids", Clin. Pharmacokinet, (1996) vol. 30, No. 5 pp. 333-358.

Han et al., "The Interaction of pH, Bile and *Helicobacter pylori* May Explain Duofenial Ulcer", American Journal of Gastroenterology (1996) vol. 91, No. 6, pp. 1135-1137.

Mohler et al., "Effect of Ursodeoxycholic Acid on HCV Replication in Subtyped Chronic Hepatitis C", Digestive Diseases and Sciences, (1996) vol. 41, No. 6 p. 1276.

Newman et al., "Starch", Analytical Profiles of Drug Substances, (1996) Bristol-Myer Squibb Pharmaceutical Research Institute, New Brunswick, NJ, pp. 523-577.

Nishigaki, et al., "Ursodeoxycholic Acid Corrects Defective Natural Killer Activity by Inhibiting Prostaglandin $E_2$ Production in Primary Biliary Cirrhosis", Digestive Diseases and Sciences, (1996) vol. 41, No. 7, pp. 1487-1493.

Panini et al., "The Influence of 2-Hydroxypropyl-β-Cyclodextrin on the Haemolysis Induced by Bile Acids", J. Pharm. Pharmacol., (1996) vol. 48 pp. 641-644.

Tanaka et al., "Ligand-Independent Activation of the Glucocorticord Receptor by Ursodeoxycholic Acid", The Journal of Immunology (1996) 156:1601-1608.

Buckley et al., "Controlled Release Drugs in Overdose Clinical Consideration", Drug Safety (1996) vol. 12, No. 1 pp. 73-84.

Jorgensen et al., "Characterisation of patients with a complete biochemical response to ursodeoxycholic acid", GUT (1995) 36:935-938.

Klumra et al., "A 1-h Topical Therapy for the Treatment of *Helicobacter pylori* Infection", Am. J. Gastercenterol. (1995) vol. 90, No. 1, pp. 60-63.

Lindor et al., "The Combination of Ursodeoxycholic Acid and Methotrexate for Patients with Primary Biliary Cirrhosis: The Results of a Pilot Study", HEPATOLOGY (1995) vol. 22, No. 4 pp. 1158-1162.

Rodrigues et al., "The Site-Specific Delivery of Ursodeoxycholic Acid to the Rat Colon by Sulfate Conjugation", Gastroenterology (1995) vol. 109 pp. 1835-1844.

Simoni et al., "Bioavailability Study of a New, Sinking, Enteric-Coated Ursodeoxycholic Acid Formulation", Pharmacological Research (1995) vol. 31, No. 2 pp. 115-119.

P.J. Sinko, "Utility of Pharmacodynamic Measures for Assessing the Oral Bioavailability of Peptides. I. Administration of Recombinant Salmon Calcitonin in Rats", Journal of Pharmaceutical Sciences, (1995) vol. 84, No. 11, pp. 1374-1378.

A. Benjamin Suttle and Kim L. R. Brouwer, "Regional Gastronintestinal Absorption of Ranitidine in the Rat", Pharmaceutical Research, (1995) vol. 12, No. 9 pp. 1311-1315.

R. Panini et al., "Improvement of Ursodeoxycholic Acid Bioavailability by 2-Hydroxypropyl-β-Cyclodextrin Complexation in Healthy Volunteers", Pharmacological Research, (1995) vol. 31, No. 314 pp. 205-209.

"Pharmaceutical Necessities", Remington: The Science and Practice of Pharmacy, Mack Printing Co., Easton, Pennsylvania (1995) pp. 1409-1410.

Angelin et al., "Effects of Ursodeoxycholic Acid on Plasma Lipids", Scand J. Gastroenterol. (1994) 29 Suppl 204:24-26.

I. Björkhem, "Inborn Errors of Metabolism with Consequences for Bile Acid Biosynthesis: A Minireview", Scand J. Gastroenteral (1994) 29 Suppl. 204:68-72.

A. Björkland and T.H. Totterman, "Is Primary Biliary Cirrhosis an Autoimmune Disease?", Scand J. Gastroenteral (1994) 29 Suppl. 204:32-9.

Boberg et al., "Etiology and Pathogenesis in Primary Sclerosing Cholangitis", Scand J. Gastroenterol. (1994) 29 Suppl. 204:47-58.

Cirillo N.W. and F.R. Zwas., "Ursodeoxycholic Acid in the Treatment of Chronic Liver Disease", Am J Gastroenterol (1994) vol. 89, No. 9 pp. 1447-1452.

K. Einarsson, "Effect of Urodeoxycholic Acid on Hepatic Cholesterol Metabolism", Scand J. Gastroenteral (1994) 29 Suppl. 204:19-23.

Kurt Einarsson, Ed., "Treatment with Ursodeoxycholic Acid in Clinical Hepatology", Proceedings of a Workshop Held Feb. 3-4, 1994 in Goteborg, Sweden, Scandinavian University Press (1994) pp. 1-72.

S. Friman and J Svarik, "A Possible Role of Ursodeoxycholic Acid in Liver Transplantation", Scand J. Gastroenteral (1994) 29 Suppl. 204:62-4.

A.F. Hofmann, "Pharmacology of Ursodeoxycholic Acid, an Enterohepatic Drug", Scand J. Gastroenteral (1994) 29 Suppl. 204:1-15.

U. Leuschner et al., "Ursodeoxycholic Acid Therapy in Primary Biliary Cirrhosis", Scand J. Gastroenteral (1994) 29 Suppl. 204:40-6.

Lindor et al., "Ursodeoxycholic Acid in the Treatment of Primary Biliary Cirrhosis", Scand J. Gastroenteral (1994) 106:1284-1290.

McLeod et al., "Glucocorticoid-Dextran Conjugates as Potential Prodrugs for Colon-Specific Delivery: Hydrolysis in Rat Gastrointestinal Tract Contents", J. Pharm Sci., (1994) vol. 83, No. 9., pp. 1284-1288.

McLeod et al., "Glucocorticoid-Dextran Conjugates as Potential Prodrugs for Colon-Specific Delivery: Steady-State Pharamcokinetics in the Rat", Biopharmaceutics & Drug Disposition, (1994) vol. 15 pp. 151-161.

Paumgartner et al., "Ursodeoxycholic Acid Treatment of Cholesterol Gallstone Disease", Scand J. Gastroenteral (1994) 29 Suppl 204: 28-31.

Poupon, et al., "Ursodiol For the Long-Term Treatment of Primary Billary Cirrhosis", The New England Journal of Medicine, (1994) vol. 330, No. 19, pp. 1342-1347.

Roda et al., "Improved Intestinal Absorption of an Enteric-Coated Sodium Ursodeoxycholate Formulation", Pharmaceutical Research, (1994) vol. 11, No. 5 pp. 642-647.

Roda et al., "Influence of Ursodeoxycholic Acid on Biliary Lipids", Scand J Gastroenterol (1994) 29 Suppl. 204:16-8.

A. Stiehl, "Ursodeoxycholic Acid Therapy in Treatment of Primary Sclerosing Cholangitis", Scand J Gastroenterol (1994) 29 Suppl. 204:59-61.

Strandvik et al., "Cystic Fibrosis: Is Treatment with Ursodeoxycholic Acid of Value?", Scand J Gastroenterol (1994) 29 Suppl. 204:65-7.

McLeod et al., "Synthesis and Chemical Stability of Glucocoritcoid-Dextran Esters: Potential Prodrugs for Colon-Specific Delivery", International J. of Pharmaceutics, (1993) vol. 92 pp. 105-114.

Gerrit H. P. Te Wierik et al., "Preparation, Characterization, and Pharmaceutical Application of Linear Dextrins, I. Preparation and Characterization Amylodextrin, Metastable Amylodextrins, and Metastable Amylose", Pharmaceutical Research, (1993) vol. 10, No. 9 pp. 1274-1279.

Gerritt H. P. Te Wierik et al., "Preparation, Characterization, and Pharmaceutical Application of Linear Dextrins. II. Complexation and Dispersion of Drugs with Amylodextrin by Freeze-Drying and Kneading", Pharmaceutical Research, (1993) vol. 10, No. 9 pp. 1280-1284.

G. H. P. Te Wierik et al., "Preparation, Characterization and Pharmaceutical Application of Linear Dextrins: IV. Drug Release from Capsules and Tablets Containing Amylodextrin", International J. of Pharmaceutics, (1993) vol. 98 pp. 219-224.

Scott L. Myers et al., "Solid-State Emulsions: The Effects of Maltodextrin on Microcrystalline Aging", Pharmaceutical Research, (1993) vol. 10, No. 9 pp. 1389-1391.

Dressman et al., "Gastrointestinal Parameters that Influence Oral Medications", J. of Pharmaceutical Sciences, (1993) vol. 82, No. 9 pp. 857-872.

Thorsteinn Loftsson et al., "The Effect of Cyclodextrins on the Solubility and Stability of Medroxyprogesterone Acetate and Megestrol Acetate in Aqueous Solution", International J. of Pharmaceutics, (1993) vol. 98 pp. 225-230.

Beuers et al., "Ursodeoxycholic Acid for Treatment of Primary Sclerosing Cholangitis: A Placebo-controlled Trial", Hepatology. (1992) vol. 16, No. 3, pp. 707-714.

Bode et al., "Polymorphism in *Helicobacter pylori*—a key function in recurrence of infection", Medizinische Klinik, , (1992) 87(4):179-84.

Colombo et al., "Ursodeoxycholic Acid Therapy in Cystic Fibrosis-associated Liver Disease: A Dose-response Study", HEPATOLOGY, (1992) vol. 16, No. 4 pp. 924-930.

De Caprio et al., "Bile Acid and sterol solubilization in 2-hydroxypropyl-β-cyclodextrin", Journal of Lipid Research, (1992) vol. 33, pp. 441-443.

Fried et al., "Ursodeoxycholic Acid Treatment of Refractory Chronic Graft-versus-Host Disease of the Liver", Annals of Internal Medicine, (1992) 116:624-629.

Walker et al., "Intestinal Absorpotion of Ursodeoxycholic Acid in Patients With Extrahepatic Biliary Obstruction and Bile Drainage", Gastroenterology (1992) 102:810-815.

M.L. Hanninen, "Sensitivity of *Helicobacter pylori* to Different Bile Salts", Eur. J. Clin. Microbiol. Infect., (1991) vol. 10, pp. 515-518.

Mathai et al., "The effect of bile acids on the growth and adherence of *Helicobacter pylori*", Aliment Pharmacol Therap. (1991) 5, pp. 653-668.

Rolandi et al., "Effects of ursodeoxycholic acid (UDCA) on serum liver damage indices in patients with chronic active hepatitis", Eur J. Clin Pharmacol (1991) 40:473-476.

Tan et al., "Studies on Complexation between β-Cyclodextrin and Bile Salts", International J. Pharmaceutics, (1991) vol. 74 pp. 127-135.

G. Buck. "*Campylobacter pylori* and Gastrroduodenal Disease", Clinical Microbiology Reviews, (1990) vol. 3, No. 1 pp. 1-12.

Chazouilleres et al., "Ursodeoycholic Acid for Primary Sclerosing Cholangitis", J. HEPATOLOGY, (1990) vol. 11 pp. 120-123.

Colombo et al., "Effects of Ursodeoxycholic Acid Therapy for Liver Disease Associated with Cystic Fibrosis", J. of Pediatrics, (1990) vol. 117, No. 3 pp. 482-489.

M. Y. Morgan, "Branched Chain Amino Acids in the Management of Chronic Liver Disease Facts and Fantasies", J. of Hepatology, (1990) vol. 11 pp. 133-141.

Podda et al., "Effect of Different Doses of Ursofeoxycholic Acid in Chronic Liver Disease", Digestive Diseases and Sciences, (1989) vol. 34, No. 12, Suppl. pp. 59S-65S.

Aigner A and Bauer A, "Bile acids, Long known active substances with a future", Med Monatsschr Pharm (1988) (11): 369-75.

Dioguardi et al., "The role of oral branched-chain amino acids (BCAAs) in the elevation of plasma ammonia (pNH$_3$)", Chapter 68, in Advances in Ammonia Metabolism and Hepatic Encephalopathy, Soeters et al., eds., (1988) Elsevier Science Publishers B.V., pp. 527-533.

Montanari et al., "Oral administration of branched-chain amino acids (BCAAs) in liver cirrhosis (LC): effect on their intra- and extracellular pools", Chapter 67, in Advances in Ammonia Metabolism and Hepatic Encephalopathy, Soeters et al., eds., (1988) Elsevier Science Publishers B.V., pp. 519-526.

N.F.H. Ho, "Utilizing Bile Acid Carrier Mechanisms to Enhance Liver an Small Intestin Absorption", Annais New York Academy of Sciences, (1987) 507:315-29.

Fiaccadori et al., "The effect of dietary supplementation with branch-chain amino acids (BCAAs) vs. casein in patients with chronic recurrent portal systemic encephalopathy: a controlled trial", pp. 489-497. (1988) Elsevier Science Publishers B.V. Advances in ammonia metabolism and hepatic encephalopathy.

D.S. Tompkins and AP West. "Campylobacterpylori, acid and bile", J. Clin. Pathol. (1987) 40:1387.

Van Caekenberghe et al., "In Vitro Synergistic Activity between Bismuth Subcitrate and Various Antimicrobial Agents against Campylobacter pylorids", Antimicrobial Agent and Chemotherapy, (1987) vol. 31, No. 9, pp. 1429-1430.

Miyajima et al., "Interaction of β-Cyclodextrin with Bile Salts in Aqueos Solutions", Chem. Pharm. Bull., (1986) vol. 34, No. 3 pp. 1395-1398.

Golub et al., "Physiologic Considerations in Drug Absorption from the Gastrointestinal Tract", J. Allergy Clin. Immunol., (1986) vol. 78, No. 4, Part 2 pp. 689-694.

Gordon et al., "Nasal Absorption of Insulin: Enhancement by Hydrophobic Bile Salts", Proc. Natl. Acad. Sci., (1985) vol. 82 pp. 7419-7423.

Parquet et al., "Bioavailability, Gastrointestinal Transit, Solubilization and Faecal Excretion of Ursodeoxycholic Acid in Man", European J. of Clinical Investigation, (1985) vol. 15 pp. 171-178.

Stefaniwsky et al., "Ursodeoxycholic Acid Treatment of Bile Reflux Gastritis", GASTROENTEROLOGY (1985)vol. 89, pp. 1000-1004.

K. Müller, "Structural Aspects of Bile Salt-Lecithin Mixed Micelles", HEPATOLOGY, (1984) vol. 4, No. 5 pp. 134S-137S.

Murakami et al., "Effect of Bile Salts on the Rectal Absorption of Sodium Ampicillin in Rats", Chem. Pharm. Bull., (1984) vol. 32, No. 5 pp. 1948-1955.

Zentler-Munro et al., "Effect of Intrajejunal Acidity on Aqueous Phase Bile Acid and Lipid Concentrations in Pancreatic Steatorrhoea Due to Cystic Fibrosis", GUT (1984) vol. 25 pp. 500-507.

Moses et al., "Insulin Administered Intranasally as an Insulin-Bile Salt Aerosol Effectiveness and Reproducibility in Normal and Diabetic Subjects", DIABETES, (1983) vol. 32 pp. 1040-1047.

Ziv et al., "Bile Salts Facilitate the Absorption of Heparin from the Intestine", Biochemical Pharmacology, (1983) vol. 32, No. 5 pp. 773-776.

Armstrong et al., "The Hydrophobic-Hydrophilic Balance of Bile Salts. Inverse Correlation between Reverse-Phase High Performance Liquid Chromatographic Mobilities and Micellar Cholesterol-Solubilizing Capacities", J. Lipid Research, (1982) vol. 23 pp. 70-80.

Podda et al., "Gallstone Dissolution After 6 Months of Ursodeoxycholic Acid (UDCA): Effectiveness of Different Doses", J. Int. Med Res. (1982) vol. 10 pp. 59-63.

Hirai et al., "Effect of Surfactants on the Nasal Absorption of Insulin in Rats", International J. of Pharmaceutics, (1981) vol. 9 pp. 165-172.

Hirai et al., "Mechanisms for the Enhancement of the Nasal Absorption of Insulin by Surfactants", International J. Phamaceutics, (1981) vol. 9 pp. 173-184.

Hollander et al., "Intestinal Absorption of Aspirin, Influence of pH, Taurocholate, Ascorbate and Ethanol", J. Lab. Clin. Med., (1981) vol. 98, No. 4 pp. 591-595.

Reynier et al., "Comparative Effects of Cholic, Chenodeoxycholic, and Ursodeoxycholic Acids on Micellar Solubilization and Intestinal Absorption of Cholesterol", J. Lipid Research, (1981) vol. 22 pp. 467-473.

Igimi et al., "pH-Solubility Relations of Chenodeoxycholic and Ursodeoxycholic Acids: Physical-Chemical Basis for Dissimilar Solution and Membrane Phenomena", J. Lipid Research, (1980) vol. 21 pp. 72-90.

Carey et al., "Micelle Formation by Bile Salts", Arch Intern Med, (1972) vol. 130, pp. 506-527.

Matthew J. Mollan, Jr. et al., "One of Aqueous Soluble Starch Conversion Products", MALTODEXTRIN, N/D, pp. 308-349.

"Maltrin® Maltodextrins & Corn Syrup Solids Chemical and Physical Properties", GPC Technical Bulletin, TB31-021296, Grain Processing Corp., Muscatine, Iowa, N/D, Brochure + 4 pages.

"Saccharide Composition Typical Carbohydrate Profiles", GPC Technical Bulletin TB30-021296, Grain Processing Corp., Muscatine, Iowa, N/D, 1 page.

"Decarbazine", Aidsmap Treatment and Care, http://www.aidsmap.com/en/docs/9685F4D7-D57C-4F10-AA1F-D5EDF7811B3A.asp, p. 1 [Exhibit 1].

"Drug Information: Decarbazine", Medline Plus, http://www.nlm.nih.gov/medlineplus/druginfo/medmaster/a682750.html, p. 2 [Exhibit 2].

"Dacarbazine", NCI Terminology Browser, http://nciterms.ncl.nih.gov/NCIBrowser/PrintableReport.jsp?dictionary=NCI_Thesaurus&code=C411, p. 3 [Exhibit 3].

P.J. Neveu, "The Effects of Thiol Moiety of Levamisole on Both Cellular and Humoral Immunity During the Early Response to a Hapten-Carrier Complex" Clin. Exp. Immunol. vol. 32, pp. 419-422 [Exhibit 4].

E. Nagy et al., "Imuthiol Inhibits the Etoposide-Induced Apoptosis in HL-60 Cells" Immunology Letters vol. 64, pp. 1-4 [Exhibit 5].

"An Assessment of the In Vivo Biological Effects of Diethyidithiocarbamate (DTC) in HIV-Infected Patients", ClinicalTrials.gov, http://www.clinicaltrials.gov/ct/showNCT00000650jsessionid=AF8903A542A345FA86641E2A559AC8C9?order=1, p. 6 [Exhibit 6].

Hubner et al., "Enhancement of Monocyte Antimycobacterial Activity by Diethyldithiocarbamate (DTC)" Int. J. Immunopharmac. vol. 13, pp. 1067-1072 [Exhibit 7].

"Diethyldithiocarbamate", http://nciterms.nci.nih.gov/NCIBrowser/ConceptReports.jsp?, p. 2 [Exhibit 8].

"Proventil", PDR Health, http://www.pdrhealth.com/drug_info/rxdrugprofiles/drugs/pro1360.shtml, p. 5.

"Powered by Dorland's Illustrated Medical Dictionary: E", MerckSource, http://www.mercksource.com/pp/us/cns//cns_hl_dorlands.jspzQzpgzEzzSzppdocszSzuszSzcommonzSzdorlandsz SzdorlandzSzdmd_e_17zPzhtm, p. 3.

F.S. Giorgi et al., "The role of norepinephrine in epilepsy: from the bench to the bedside" Neurosci. Behavioral. Rev.. vol. 28, pp. 507-524.

K. Bodin et al., "Antiepileptic drugs increase plasma levels of 4-β-hydroxycholesterol in humans: evidence for Involvement of cytochrome p450 3A4" J. Biol. Chem. vol. 276, pp. 38685-38689.

V.S. Kasture et al., "Anticonvulsant activity of Albizzia lebbeck leaves" Indian Journal of Experimental Biology vol. 34, pp. 78-80.

V.S. Kasture et al., "Anticonvulsive activity of Albizzia lebbeck, Hibiscus rosa sinesis and Butea monosperma in experimental animals" Journal of Ethnopharmacology vol. 71, pp. 65-75.

P.P. But et al., "Ethnopharmacology of bear gall bladder: I" Journal of Ethnopharmacology vol. 47, pp. 27-31.

K.G. Rajesh et al., "Hydrophilic Bile Salt Ursodeoxycholic Acid Protects Myocardium Against Reperfusion Injury in a PI3K/Akt Dependent Pathway", Journal of Molecular and Cellular Cardiology, vol. 39, pp. 766-776.

Cecilia M.P. Rodrigues et al., "Ursodeoxycholic Acid May Inhibit Deoxycholic Acid-Induced Apoptosis by Modulating Mitochondrial Transmembrane Potential and Reactive Oxygen Species Production", Molecular Medicine, vol. 4, pp. 165-178.

"Drug Information: Hydralazine", Medline Plus, http://www.nlm.nih.gov/medlineplus/druginfo/medmaster/a682246.html, p. 3.

"Drug Information: Isoxsuprine (Systemic)", Medline Plus, http://www.nlm.nih.gov/medlineplus/druginfo/uspdi/202310.html , p. 4.

"Drug Information: Nyldrin (Systemic)", Medline Plus, http://www.nlm.nih.gov/medlineplus/druginfo/uspdi/202416.html , p. 3.

"Drug Information: Dyphyline (Systemic)", Medline Plus, http://www.nlm.nih.gov/medlineplus/druginfo/uspdi/202752.html , p. 4.

"Drug Information: Bronchodilators, Andrenergic (Inhalation)", Medline Plus, http://www.nlm.nih.gov/medlineplus/druginfo/uspdi/202095.html , p. 12.

"Colfosceril Palmitate", Tiscali, http://www.tiscali.co.uk/lifestyle/healthfitness/health_advice/netdoctor/archive/100003422.html , p. 2.

"Selenium", PDR Health, http://www.pdrhealth.com/drug_info/nmdrugprofiles/nutsupdrugs/sel_0232.shtml, p. 8.

"Clean, Beautiful, Healthy Life", LG Household & Health Care, http://www.lgcare.com/english/aboutus/06.html, p. 3.

"Zovirax", PDRhealth, http://www.pdrhealth.com/drug_info/rxdrugprofiles/drugs/zov1505.shtml , p. 4.

"Denavir", PDRhealth, http://www.pdrhealth.com/drug_info/rxdrugprofiles/drugs/den1123.shtml , p. 2.

V. Fontes et al., "Recurrent Aphthous Stomatitis: Treatment With Colchicine. An Open Trial of 54 Cases", Ann. Dermatol. Vepereol. vol. 129, pp. 1365-1369 , (with abstract).

"Drug Information: Celecoxib", Medline Plus, http://www.nlm.nih.gov/medlineplus/druginfo/medmaster/a699022.html , p. 4.

R.L. Wynn, "New Reports on Dental Analgesics. NSAIDs and Cardiovascular Effects, Celecoxib for Dental Pain, and a New Analgesic–Tramadol With Acetaminophen" General Dentistry vol. 50, pp. 218-220, 222.

R.L. Wynn, "Update on Nonprescription Pain Relievers for Dental Pain", General Dentistry vol. 52, pp. 94-98.

P.M. Preshaw et al., "Self-medication for the control of dental pain: what are our patients taking?", Dent Update vol. 21, pp. 299-301, 304.

A.D. McNaught, "Nomenclature of Carbohydrates", Pure and Applied Chemistry, vol. 68, pp. 1919-2008.

D.L. Nelson, "Carbohydrates and Glycobiology", Lehninger Principles of Biochemistry, Fourth Edition, pp. 238-271.

H.R. Horton, "Carbohydrates", Principles of Biochemistry, Second edition, pp. 228-234.

Gerhard Schmid, "Preperation and Industrial Production of Cyclodextrins", Comprehensive Supramolecular Chemistry, vol. 3, pp. 41-56.

Frömming, "Cyclodextrins", Cyclodextrins in Pharmacy, Chapter 1, pp. 1-18.

Frömming, "Cyclodextrin Derivatives", Cyclodextrins in Pharmacy, Chapter 2, pp. 19-32.

Lehninger et al., "Carbohydrates and Glycobiology", Principles of Biochemistry, pp. 301-307.

D.S. Alberts et al., "Phase III Trial of Ursodeoxycholic Acid to Prevent Colorectal Adenoma Recurrence", Journal of National Cancer Institute, vol. 97, No. 11, pp. 846-853.

Kirk et al.; "Inclusion Compounds", Encyclopedia of Chemical Technology, Fourth Edition; vol. 14; pp. 125-135.

* cited by examiner

H. pylori cultured from Columbia medium pictured by
Transmission Electron Microscope 48hrs, after H. pylori treated with UDCA & bismuth citrate
pictured by Transmission Electron Microscope 72hrs, after H. pylori treated with UDCA & bismuth citrate
pictured by Transmission Electron Microscope

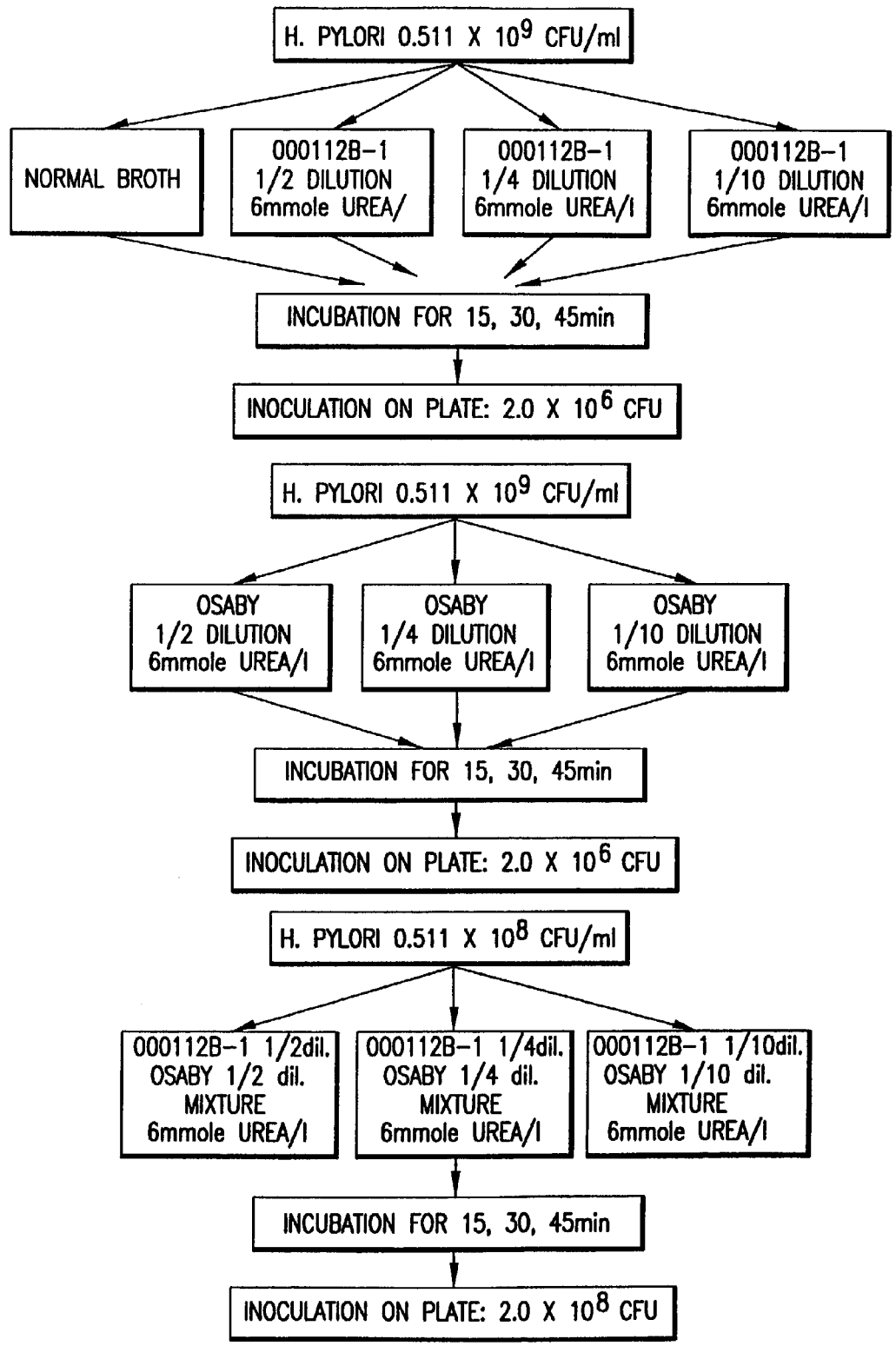
FIG.11 PLATES WERE INCUBATED MICROAEROPHILICALLY AT 37°C FOR 72 HOURS.

PREPARATION OF AQUEOUS CLEAR SOLUTION DOSAGE FORMS WITH BILE ACIDS

CROSS-REFERENCE TO RELATED APPLICATION

This application is a divisional application of U.S. patent application Ser. No. 09/778,154, filed Feb. 5, 2001, which claims the benefit of U.S. provisional application Ser. No. 60/180,268, filed Feb. 4, 2000 and is a continuation-in-part application of U.S. patent application Ser. No. 09/357,549, filed Jul. 20, 1999, now U.S. Pat. No. 6,251,428, which claims the benefit of U.S. provisional application Ser. No. 60/094,069, filed Jul. 24, 1998.

BACKGROUND OF THE INVENTION

Bile acids salts which are organic acids derived from cholesterol are natural ionic detergents that play a pivotal role in the absorption, transport, and secretion of lipids. In bile acid chemistry, the steroid nucleus of a bile acid salt has the perhydrocyclopentano phenanthrene nucleus common to all perhydrosteroids. Distinguishing characteristics of bile acids include a saturated 19-carbon sterol nucleus, a beta-oriented hydrogen at position 5, a branched, saturated 5-carbon side chain terminating in a carboxylic acid, and an alpha-oriented hydroxyl group in the 3-position. The only substituent occurring in most natural bile acids is the hydroxyl group. In most mammals the hydroxyl groups are at the 3, 6, 7 or 12 positions.

The common bile acids differ primarily in the number and orientation of hydroxyl groups on the sterol ring. The term, primary bile acid refers to these synthesized de novo by the liver. In humans, the primary bile acids include cholic acid ($3\alpha$, $7\alpha$, $12\alpha$-trihydroxy-$5\beta$-cholanic acid) ("CA") and chenodeoxycholic acid ($3\alpha$, $7\alpha$-dihydroxy-$5\beta$-cholanic acid) ("CDCA"). Dehydroxylation of these bile acids by intestinal bacteria produces the more hydrophobic secondary bile acids, deoxycholic acid ($3\alpha$, $12\alpha$-dihydroxy-$5\beta$-cholanic acid) ("DCA") and lithocholic acid ($3\alpha$-hydroxy-$5\beta$-cholanic acid) ("LCA"). These four bile acids CA, CDCA, DCA, and LCA, generally constitute greater than 99 percent of the bile salt pool in humans. Secondary bile acids that have been metabolized by the liver are sometimes denoted as tertiary bile acids.

Keto-bile acids are produced secondarily in humans as a consequence of oxidation of bile acid hydroxyl groups, particularly the 7-hydroxyl group, by colonic bacteria. However, keto-bile acids are rapidly reduced by the liver to the corresponding $\alpha$ or $\beta$-hydroxy bile acids. For example, the corresponding keto bile acid of a CDCA is 7-keto lithocholic acid and one of its reduction products with the corresponding $\beta$-hydroxy bile acid is ursodeoxycholic acid ($3\alpha$-$7\beta$-dihydroxy-$5\beta$-cholanic acid) ("UDCA"), a tertiary bile acid.

UDCA, a major component of bear bile, has been used for the treatment of and the protection against many types of liver disease for a little over 70 years as a major pharmaceutical agent. Its medicinal uses include the dissolution of radiolucent gall stones, the treatment of biliary dyspepsias, primarily biliary cirrhosis, primary sclerosing choplangitis, chronic active hepatitis and hepatitis C. In other mammalian species, bile acids containing a $6\beta$-hydroxyl group, which are found in rats and mice, are known as muricholic acid; $6\alpha$-hydroxy bile acids produced by swine are termed hyocholic acid and hyodeoxycholic acids. 23-hydroxy bile acids of aquatic mammals are known as phocecholic and phocedeoxycholic acids.

Typically, more than 99 percent of naturally occurring bile salts secreted into human bile are conjugated. Conjugates are bile acids in which a second organic substituent (e.g. glycine, taurine, glucuronate, sulfate or, rarely, other substituents) is attached to the side chain carboxylic acid or to one of the ring hydroxyl groups via an ester, ether, or amide linkage. Therefore, the ionization properties of conjugated bile acids with glycine or taurine are determined by the acidity of the glycine or taurine substituent.

Free, unconjugated, bile acid monomers have $pK_a$ values of approximately 5.0. However, $pK_a$ values of glycine conjugated bile acids are on average 3.9, and the $pK_a$ of taurine conjugate bile acids are less than 1.0. The effect of conjugation, therefore, is to reduce the $pK_a$ of a bile acid so that a large fraction is ionized at any given pH. Since the ionized salt form is more water soluble than the protonated acid form, conjugation enhances solubility at a low pH. Free bile acid salts precipitate from aqueous solution at pH 6.5 to 7. In contrast, precipitation of glycine conjugated bile acid occurs only at pH of less than 5. Taurine conjugated bile acids remain in aqueous solution under very strongly acidic conditions (lower than pH 1). However, in the gastric pH range, certain bile acids such as UDCA and CDCA are no longer soluble.

Conjugation of the side chain of a bile acid with glycine or taurine has little influence on the hydrophobic activity of fully ionized bile salts. More hydrophobic bile salts exhibit greater solubilizing capacity for phospholipid and cholesterol and are consequently better detergents. More hydrophobic bile salts are also more injurious to various membranes, both in vivo and in vitro.

Natural bile salt pools invariably contain multiple bile acid salts. Mixtures of two or more bile salts of differing hydrophobic activity may behave as a single bile salt of an intermediate hydrophobic activity. As a result, detergent properties and the toxicity of mixtures of two bile acids of differing hydrophobic activity often are intermediate between the individual components. Biologic functions and biologic properties of bile acids resulting from their amphiphillic properties are as follows:

1. Ursodeoxycholic acid is a useful immuno-modulating agent.
2. Ursodeoxycholic acid inhibits deoxycholic acid-induced apoptosis by modulating mitochondrial transmembrane potential and reactive oxygen species production.
3. Ursodeoxycholic acid inhibits induction of nitric oxide synthase (NOS) in human intestinal epithelial cells and in vivo.
4. The hydrophilic nature of ursodeoxycholic acid confers cytoprotection in necroinflammatory diseases of the liver.
5. Ursodeoxycholic acid significantly improves transaminases and cholestatic enzymatic indices of liver injury in chronic hepatitis.
6. Bile acids substantially inhibit the growth of *H. pylori*.
7. Ursodeoxycholic acid is the most potent pepsin inhibitor among bile acids.
8. High levels of bile acids remarkably inhibit the proliferation of hepatitis C virus.
9. Ursodeoxycholic acid has cell membrane stabilizing properties.
10. Ursodeoxycholic acid alleviates alcoholic fatty liver.
11. Ursodeoxycholic acid has a vasodilative effect on the systemic vascular bed but altered neither pulmonary vascular function nor cardiac functions.

12. Bile acid synthesis from cholesterol is one of the two principal pathways for the elimination of cholesterol from the body.
13. Bile flow is generated by the flux of bile salts passing through the liver. Bile formation represents an important pathway for solubilization and excretion of organic compounds, such as bilirubin, endogenous metabolites, such as emphipathic derivatives of steroid hormones; and a variety of drugs and other xenobiotics.
14. Secretion of bile salts into bile is coupled with the secretion of two other biliary lipids, phosphatidylcholine (lecithin) and cholesterol. Coupling bile salt output with the lecithin and cholesterol output provides a major pathway for the elimination of hepatic cholesterol.
15. Bile salts, along with lecithin, solubilize cholesterol in bile in the form of mixed micelles and vesicles. Bile salt deficiency, and consequently reduced cholesterol solubility in bile, may play a role in the pathogenesis of cholesterol gallstones.
16. Bile acids are thought to be a factor in the regulation of cholesterol synthesis. At present, it is not certain whether they regulate the cholesterol synthesis by acting directly on the hydroxymethylglutaryl-coenzyme A (HMG-CoA) reductase or indirectly by modulating the cholesterol absorption in the intestine.
17. Bile salts in the enterohepatic circulation are thought to regulate the bile acid synthesis by suppressing or derepressing the activity of cholesterol 7-hydroxylase, which is the rate-limiting enzyme in the bile acid biosynthesis pathway.
18. Bile acids may play a role in the regulation of hepatic lipoprotein receptors (apo B.E.) and consequently may modulate the rate of uptake of lipoprotein cholesterol by the liver.
19. In the intestines, bile salts in the form of mixed micelles participate in the intraluminal solubilization, transport, and absorption of cholesterol, fat-soluble vitamins, and other lipids.
20. Bile salts may be involved in the transport of calcium and iron from the intestinal lumen to the brush border.

Recent drug delivery research concerning the characteristics and biofunctions of naturally occurring bile acid as an adjuvant and/or a carrier has focused on the derivatives and analogs of bile acids and bile acids themselves as novel drug delivery systems for delivery to the intestinal tract and the liver. These systems exploit the active transport mechanism to deliver drug molecules to a specific target tissue by oral or cystic administration. Thus, if bile acids or bile acid derivatives are rapidly and efficiently absorbed in the liver and, consequently, undergo enterohepatic cycling, many potential therapeutic applications are foreseen including the following: improvement of the oral absorption of an intrinsically, biologically active, but poorly absorbed hydrophillic and hydrophobic drug; liver site-directed delivery of a drug to bring about high therapeutic concentrations in the diseased liver with the minimization of general toxic reactions elsewhere in the body; and gallbladder-site delivery systems of cholecystographic agents and cholesterol gallstone dissolution accelerators. As an example, in 1985, Drs. Gordon & Moses et al. demonstrated that a therapeutically useful amount of insulin is absorbed by the nasal mucosa of human beings when administered as a nasal spray with common bile salts such as DCA, UDCA, CDCA, CA, TUDCA, and TCDCA. See Moses, Alan C., et al., *Diabetes* vol. 32 (November 1983) 1040–1047; Gordon, G. S., et al., *Proc. Nat'l Acad. Sci. USA,* vol. 82 (November 1985) 7419–7423. In their experiment, bile acids produced marked elevations in serum insulin concentration, and about 50 percent decreases in blood glucose concentrations. However, this revolutionary nasal spray solution dosage form with bile acids (salts) as an adjuvant could not be developed further and commercialized, because the nasal spray solution must be prepared immediately prior to use due to the precipitation of bile acid salt and the instability of insulin at pH levels between 7.4 and 7.8. Moreover, as indicated in this disclosure, ursodeoxycholic acid as an adjuvant could not be used because of its insolubility at pH between 7.4 and 7.8.

Bile acid salts and insulin, thus, appear to be chemically and physically incompatible. The pH of commercial insulin injection solutions is between 2.5 and 3.5 for acidified dosage forms and is between 7.00 and 7.4 for neutral dosage forms. Dosage forms of bile acid salts prepared by conventional techniques have been unable to overcome problems with bile precipitation at these pH levels and insulin is unstable at a pH of 7.4 or higher. Therefore, safe and efficient preparations of any solution dosage forms of insulin with bile acid (salt) are not commercially available at this time.

Heparin, a most potent anticoagulant, is widely used in the treatment of and in the prevention of thromboembolism. However, heparin treatment is usually limited to hospitalized patients since this drug is given only by injection. Alternate routes which have been attempted are an intrapulmonary spray, suppositories, and enema. According to numerous publications, for heparin absorption through the gastrointestinal mucosa to be facilitated, the preparations should be in acidic condition. According to Dr. Ziv, Dr. Eldor et al., heparin was absorbed through the rectal mucosa of rodents and primates only when administered in solutions containing sodium cholate or sodium deoxycholate. See Ziy E. et al., *Biochemical Pharmacology,* vol. 32, No. 5, pp. 773–776 (1983). However, heparin is only stable under acidic conditions. Bile acids are particularly not soluble in acidic conditions. Therefore, due to their incompatible characteristics, commercial dosage forms of bile acids with heparin are not presently available.

Drug delivery systems involving bile acids can provide liver-specific drug targeting which is of major interest for drug development since standard pharmacological approaches to liver diseases have been frustrated by the inadequate delivery of active agents into liver cells as well as non specific toxicity towards other organs. For example, the liver-specific delivery of a drug is necessary for inhibitors of collagen synthesis for the treatment for liver fibrosis in order to avoid unspecific and undesired side-effects in extrahepatic tissues. Furthermore, for the treatment of cancer of the biliary system, high drug levels must be achieved in the liver and the biliary system, whereas in extrahepatic tissues low drug concentrations are desired to minimize the cytoxicity of the cytostatics to normal non-tumor cells. Dr. Kramer, Dr. Wess et al. demonstrate that hybrid molecules formed by covalent linkages of a drug to a modified bile acid molecule are recognized by the Na+-dependent bile acid uptake systems in the liver and the ileum. See U.S. Pat. No. 5,641,767. Even if bile acid salts and their derivatives act as shuttles for specific delivery of a drug to the liver, as already mentioned above, there are enormous risks to the development of the derivatives of bile acids or bile acid salts as carriers because new derivatives of bile acids or bile acid salts formed by covalent linkages of a drug to bile acid must be tested for its pharmacology, toxicity and clinical effectiveness. Thus, the development of preparations in which a drug can be absorbed with bile acids or bile acid salts from the places which contain the excessive bile acids in the intestine is far easier and far more valuable than the development of the new bile acid derivatives because less testing is required.

In spite of the extremely valuable therapeutic activities and the long historic medical uses of bile acids as therapeutically active agents and as carriers and/or adjuvants based on the already mentioned biological properties and functions of bile acids, the commercial administration of bile acids is limited to pharmaceutical formulations with a solid form of bile acid which are in tablet, capsule and suspension. This is due to the insolubility of bile acid in aqueous media at pH from approximately 1 to 8. This is also due to bile's extremely bitter taste and equally bitter after-taste which lasts several hours. Ursodeoxycholic acid, chenodeoxycholic acid, and lithocholic acid are practically insoluble in water. Deoxycholic acid and cholic acid have solubilities of 0.24 g/L, and 0.2 g/L, respectively. Tauroursodeoxycholic acid, taurochenodeoxycholic acid, and taurocholic acid are insoluble in hydrochloric acid solution. The few aqueous dosage forms that are available are unstable, and have very limited uses because of pH control and maintenance problems. Moreover, some commercial pharmaceutical dosage forms of bile acids have been shown to have scant bioavailability as described in *European Journal of Clinical Investigation* (1985) 15, 171–178. Bile acid, especially ursodeoxycholic acid is poorly soluble in the gastro-duodeno jejunal contents of fasted subjects. From 21% to 50% of the ingested doses were recovered in solid form because of the unpredictable variations in the very slow progressive solubilization of solid ursodeoxycholic acid in the gastrointestinal track. Bile acids, particularly ursodeoxycholic acid, deoxycholic acid, chenodeoxycholic acid, cholic acid, hyodeoxycholic acid, 7-keto lithcholic acid, tauroursodeoxycholic acid, and taurochenodeoxycholic acid among others, are especially insoluble in the gastric juices and in aqueous hydrochloric acid solution. However, the solubility of bile acids increase with the increase of the pH in the intestine very slowly and incompletely, and eventually the bile acids become soluble at pH between 8 and 9.5.

To overcome this slow and inefficient absorption process in the intestine due to the incomplete and slow solubilization of bile acids, many newly developed pharmaceutical formulations have been prepared, such as delayed release dosage forms with water soluble solid bile acids which are often strongly alkaline. These newly developed pharmaceutical dosage forms are enterosoluble-gastroresistant. These enterosoluble-gastroresistant dosage forms remain intact in gastric juices in the stomach, but are dissolved and release the strongly alkaline solid bile salts of the formulations at the targeted area, within a limited time once they reach the small intestine.

These types of dosage forms, of course, showed better bioavailability than presently commercialized dosage forms as described in U.S. Pat. No. 5,380,533. However, it is extremely difficult and very costly to prepare the precise delayed release dosage forms which can release therapeutically active components by disintegration, dissolution and diffusion at the desired area within a limited time. According to U.S. Pat. No. 5,302,398, the absorption test of the gastroresistant enterosoluble dosage forms of bile acids, particularly ursodeoxycholic acid in man show that its absorption increases a value of about 40 percent in comparison with administering the same amount in current commercial dosage forms. Its maximum hematic concentrations are on average three times higher, and are reached faster than with the commercial formulations. Any dosage forms of bile acid formula must be capable of releasing bile acids in a known and consistent manner following administration to the patient. Both the rate and the extent of release are important, and should be reproducible. Ideally, the extent of release should approach 100 percent, while the rate of release should reflect the desired properties of the dosage form.

It is a well-known fact that solution dosage forms of drugs show significantly improved rates and extents of absorption, compared to the same drug formulated as a tablet, capsule, or suspension. This is because solution dosage forms are chemically and physically homogeneous solutions of two or more substances. Moreover, the specially designed solution dosage forms which can maintain the solution systems without breaking down under any pH conditions are ready to be diffused in the desired area for immediate and complete absorption, whereas tablets, capsules or delayed release formulations must invariably undergo disintegration, dissolution and diffusion at the desired area within a limited time. Unpredictable variations in the extent and rate of release of bile acids by the disintegration, dissolution and diffusion of delayed or immediate release dosage forms having pH-dependent instability result in the slow and inefficient bile absorption and reduced bioavailability.

The luminal surface of the stomach is coated with a thick layer of protective mucus. The mucus gel coating maintains a pH gradient from the intraluminal compartment to the apical membrane and is believed to contribute to the phenomenon of cytoprotection. *H. pylori* infection occurs on the luminal surface of the stomach mucosa within the mucus, on the epithelial surface, and within the gastric pints. Bacterial enzymes are believed to degrade the mucus glycoprotein network and reduce the polymers to monomers (or subunits) such that the mucus can no longer exist as a gel. In addition, mucinogenesis is reduced and the mucosa becomes susceptible to the erosive effects of acid. This condition may lead to gastritis and peptic ulcers.

Bismuth compounds have gained increasing interest in the therapeutic treatment of gastro-duodenal disorders and especially in the eradication of *Helicobacter pylori*, a bacterium thought to be involved in the etiology of the disease. Many oral preparations of bismuth have been used. The various preparations appear to differ in clinical efficacy as well as pharmacokinetics. The inorganic salts used have included subnitrate, subcarbonate, subgallate, tartarate, citrate and subsalicylate. The commercial preparations have generally been available over the counter and have often contained other compounds in addition to the bismuth salt. The commercial preparations have been used successfully in the treatment of both gastric and duodenal ulcer disease. These preparations have proved as effective as the histamine H2 antagonists in the treatment of gastric and duodenal ulcers and have been associated with lower relapse rates after cessation of therapy. The lower relapse rate after initial healing with bismuth preparations have been attributed to its ability to eradicate *H. pylori* and to moderate the gastroduodenitis associated with infection by this organism. Long-term eradication of *H. pylori* is more likely when bismuth preparation is administered along with antibiotics or antiseptics (local delivery) such as bile acids.

A variety of antibiotics and antiseptics display good activity against *H. pylori* in vitro. Yet when tested as single agents in clinical studies, they do not succeed in eradicating the organism. Failure of therapy and relapse are very common. The reason for this discrepancy between in vitro and clinical results has not been established. Possible explanations are poor penetration of the compounds into gastric mucus, destruction at acid pH, insolubility in acidic environment, and combinations thereof. Consequently, administration of high doses of antimicrobial agents on a daily basis is necessary for *H. pylori* eradication. The efficacy of this course of therapy is hindered by poor patient compliance due to adverse effects such as diarrhea, nausea, retching and breakdown of normal intestinal flora.

Another reason for incomplete eradication may be that the residence time of antimicrobial agents in the stomach is so short that effective antimicrobial concentrations cannot be achieved in the gastric mucous layer or epithelial cell surfaces where *H. pylori* exist. Therefore, eradication of *H. pylori* may be better achieved by a therapy that improves antimicrobial agent delivery for topical activity and absorption for systemic activity. However, no in vivo eradication trials with dosage forms that prolong the gastric residence times for topical activity and have the high absorption rate in the gastro-intestinal tract have been reported. The best results so far have been achieved with the combination of a non-absorbed agent with topical activity, colloidal bismuth compounds, and a well-absorbed agent with systemic activity, amoxicillin (Van Caekemberghe and Breyssens, 1987, *Antimicrobial Agent and Chemotherapy*, pp 1429–1430). But clearly, therapy for *H. pylori* infections is still suboptimal.

In addition to a bactericidal effect, some bismuth compounds have profound effects on some of the pathogenic mechanisms whereby *H. pylori* damage the mucosa. Bismuth compounds are potent and non-specific enzyme inhibitors. In vitro studies have suggested that these compounds may inhibit bacterial enzymes, including lipases, proteases, and glycosidases synthesized by *H. pylori*. Inhibition of bacteria enzymes and maintenance of an intact viscoelastic gel coating is thought to be related to the therapeutic action of bismuth compounds for *H. pylori* associated gastritis and peptic ulcers.

Bismuth compounds block the adhesion of *H. pylori* to epithelial cells. Shortly after oral administration of these compounds, the organisms were located inside, rather than underneath, the mucus gel. This was thought to result from loss of adherence to the apical membrane of the gastric epithelial cells. Bismuth, in the form of electron dense bodies, was seen to be deposited on the surface and within the bacterial cell. But unfortunately, intramucus bismuth concentrations often fall below the mean inhibitory concentration of bismuth compounds for *H. pylori*, because of the diluting effects of food, long disintegration time of commercial tablets at pH<1.1, and bismuth precipitation due to insolubility in acidic environment. Additionally, *H. pylori* inactivated by exposure to growth-inhibiting concentrations of bismuth compounds can remain viable for several hours and, therefore is capable of resuming normal growth when bismuth is removed.

The inhibitory factor(s) in bile was markedly reduced by acidification followed by centrifugation to remove precipitated glycine-conjugated bile acids and was completely eliminated by use of the bile acid-sequestering agent cholestyramine. These results are consistent with the notion that acidic conditions in the duodenal bulb would serve to precipitate inhibitory bile acids (or other inhibitory substances) and allow *H. pylori* to grow in an otherwise hostile environment. The observations related to reflux gastritis by D. Y. Graham (Osato et al., 1999, Digestive Diseases and Sciences 44(3):462–464) can be extended to possibly understand the relation between acid secretion and duodenal ulcer. Low pH in the duodenal bulb in patients with duodenal ulcer disease associated with high acid secretion, rapid gastric emptying, and local production of acid would both promote development of gastric metaplasia and precipitate the deleterious glycine-conjugated bile acids, allowing *H. pylori* to colonize and thrive.

SUMMARY OF THE INVENTION

The present invention relates to a composition which comprises (1) a bile acid, its derivative, its salt, or its conjugate with an amine, (2) water, and (3) a sufficient quantity of an aqueous soluble starch conversion product such that the bile acid and the starch conversion product remain in solution at any pH within a selected pH range.

The invention further relates to a composition which comprises (1) a bile acid, its derivative, its salt, or its conjugate with an amine, (2) water, and (3) a sufficient quantity of an aqueous soluble non-starch polysaccharide such that the bile acid and the polysaccharide remain in solution at any pH within a selected pH range.

The invention further relates to a pharmaceutical composition which comprises (1) a bile acid, its salt, or its conjugate with an amine, (2) water, (3) a pharmaceutical compound in a pharmaceutically appropriate amount, and (4) a sufficient quantity of an aqueous soluble starch conversion product or an aqueous soluble non-starch polysaccharide such that the bile acid, the pharmaceutical compound, and the carbohydrate remain in solution at any pH level within a selected pH range.

The invention further relates to solution dosage forms of bile acid compositions. Advantages of these solution dosage forms include improved bioavailability and absorbability of a bile acid. Additional advantages of solution dosage forms include improved bioavailability and absorbability of a pharmaceutical compound.

In some embodiments of the invention, a composition is provided which comprises (1) a bile acid, its derivative, its salt, or its conjugate with an amine, (2) water, and (3) a sufficient quantity of carbohydrate such that the bile acid component and the carbohydrate remain in solution at any pH within a selected pH range, wherein the carbohydrate is a combination of an aqueous soluble starch conversion product and an aqueous soluble non-starch polysaccharide. In embodiments containing both soluble non-starch polysaccharide and high molecular weight starch conversion product, the amounts of each are such that when combined together in the composition they are sufficient to allow the bile acid component, the high molecular weight starch conversion product, the soluble non-starch polysaccharide and the pharmaceutical compound, if any, to remain in solution at any pH within a selected pH range.

In some embodiments of the invention, a combination therapy composition is provided which may increase intensity of response to or efficacy of a pharmaceutical. Such a composition may permit administration of lower dosages of a pharmaceutical compound, attack a disease complex at different points, affect elimination and/or alter absorption of a pharmaceutical compound. Such a composition may lead to or contribute to a reduction in toxicity and/or side effects of a pharmaceutical.

The invention further relates to a composition which comprises (1) a bile acid, its salt, or its conjugate with an amine, (2) water, (3) an aqueous soluble bismuth compound, and (4) a sufficient quantity of an aqueous soluble starch conversion product or an aqueous soluble non-starch polysaccharide such that the bile acid, such that the bile acid, bismuth, and carbohydrate remain in solution at any pH level within a selected pH range.

The invention further relates to a method of treating or preventing a human or animal disease comprising administration of a composition of the invention.

BRIEF DESCRIPTION OF THE DRAWINGS

FIG. 11: *H. pylori* culture method.

DETAILED DESCRIPTION OF THE INVENTION

Figure 1:
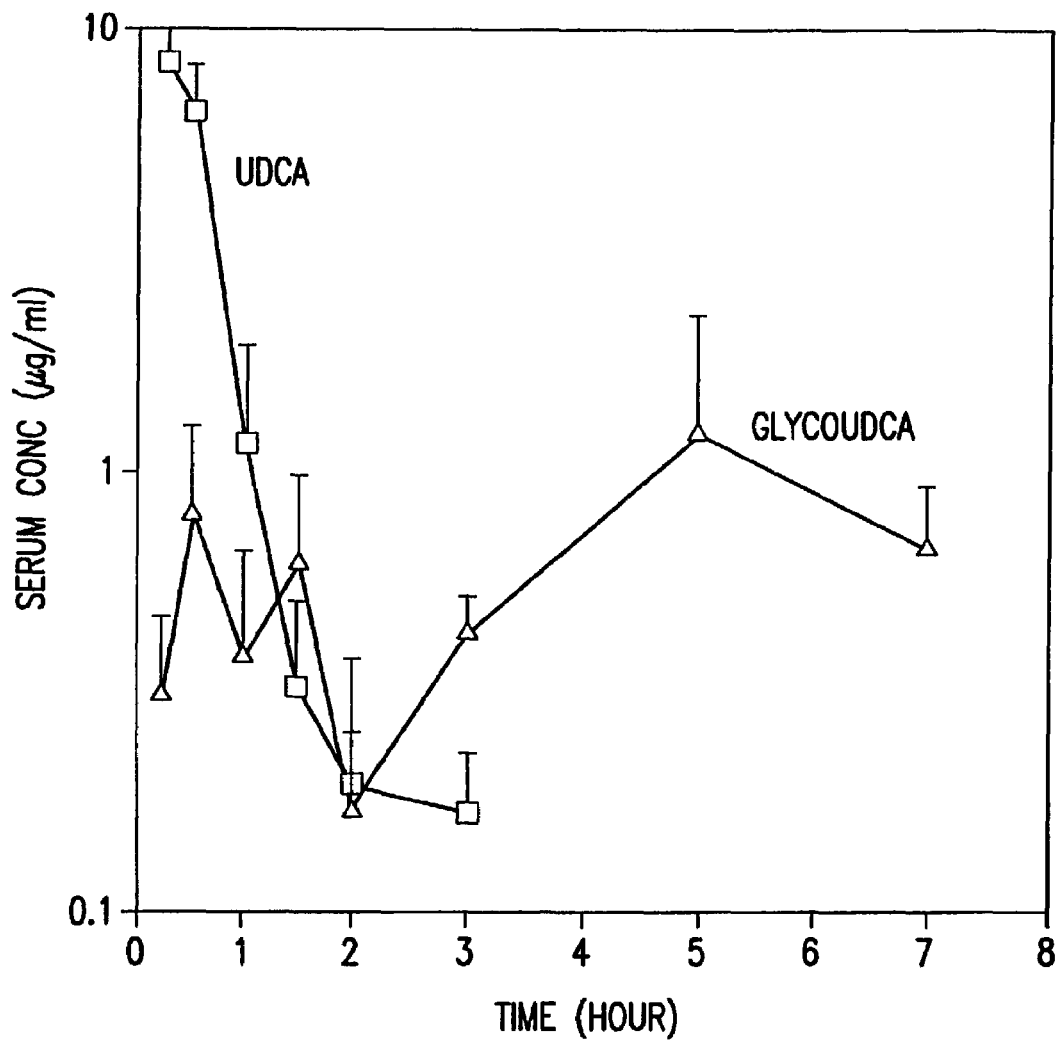
FIG. 1: Graph of blood serum—concentration of UDCA (squares) and GUDCA (triangles) versus time following administration of dosage formulations according to Examples II and VI and Table 4.

The present invention relates to an aqueous solution comprising (i) one or more soluble bile acids, aqueous soluble bile acid derivatives, bile acid salts, or bile acid conjugated with an amine, (collectively "bile acid"), (ii) water, and (iii) one or more aqueous soluble starch conversion products or aqueous soluble non-starch polysaccharide in an amount sufficient to produce a solution which does not form a precipitate at any pH within a desired pH range. In a preferred embodiment of the invention, the bile acid and the carbohydrate do not precipitate between about pH 1 and about pH 10, more preferably between about pH 1 and about pH 14, and most preferably at all pH values obtainable in an aqueous system. In some embodiments of the invention, a bile acid remains dissolved under acidic conditions as a free bile acid in spite of the general insolubility of bile acids under acidic conditions. In some embodiments of the invention, the composition may be used as a pharmaceutical formulation wherein the pharmaceutical compound remains in solution without precipitation at prevailing pH levels in the mouth, stomach and intestines. The composition may contain a bile acid or its salt which itself has pharmaceutical effectiveness. Formulations of the invention may act as a carrier, an adjuvant or enhancer for the delivery of a pharmaceutical material which remains dissolved in the composition of the invention across the desired pH range. In some embodiments of the invention, a non-bile acid pharmaceutical is used though not in solution.

It is an advantage of this invention that the bile acid and the carbohydrate remain in solution without precipitation at any pH from acidic to alkaline. These aqueous solution systems of bile acid are substantially free of precipitate or particles. A further advantage of this invention is that the aqueous solution systems demonstrate no changes in physical appearance such as changes in clarity, color or odor following the addition of strong acids or alkali even after several months observation under accelerated conditions of storage at 50° C.

In some embodiments of the invention, an aqueous solution system of bile acid is administered orally whereupon it reaches the intestine through the gastrointestinal track without precipitation of bile acids as solids by exposure to acidic gastric juices and alkaline juices of the intestine. These dissolved bile acid formulations demonstrate intact solution systems in the intestine can be effectively and completely absorbed and, consequently, undergo enterohepatic cycling. According to the invention, bile acid solubility (e.g. precipitation and changes in physical appearance) is unaffected by whether a carboxylic acid side chain of certain bile acids can be protonated (non-ionized), ionized, or a simple carboxylic acid.

The ionization state of a bile acid carboxylic acid side chain greatly effects the hydrophobicity and the hydrophilicity of the bile acid in these aqueous solution systems. In some embodiments of the invention, that ionization state is manipulated by adjusting the pH to control the toxicity, absorption, and amphiphilicity of bile acids. One or more bile acid may be dissolved in these aqueous solution systems as a therapeutically active agent, as an adjuvant of a drug, as a carrier of drug or as an enhancer of drug solubility. These aqueous solution systems may be prepared for oral consumption, enemas, mouthwashes, gargles, nasal preparations, otic preparations, injections, douches, topical skin preparations, other topical preparations, and cosmetic preparations which have a desired pH without the disadvantage of precipitation or deterioration in physical appearance after long periods of time.

Soluble bile acids are any type of aqueous soluble bile acids. A bile acid salt is any aqueous soluble salt of a bile acid. The soluble bile acid derivatives of this invention are those derivatives which are as soluble or more soluble in aqueous solution than is the corresponding underivatized bile acid. Bile acid derivatives include, but are not limited to derivatives formed at the hydroxyl and carboxylic acid groups of the bile acid with other functional groups including but not limited to halogens and amino groups. Aqueous dissolved salts of bile acids may be formed by the reaction of bile acids described above and an amine including but not limited to aliphatic free amines such as trientine, diethylene triamine, tetraethylene pentamine, and basic amino acids such as arginine, lysine, ornithine, and ammonia, and amino sugars such as D-glucamine, N-alkylglucamines, and quaternary ammonium derivatives such as choline, heterocyclic amines such as piperazine, N-alkylpiperazine, piperidine, N-alkylpiperidine, morpholine, N-alkylmorphline, pyrrolidine, triethanolamine, and trimethanolamine. According to the invention, aqueous soluble metal salts of bile acids, inclusion compound between the bile acid and cyclodextrin and its derivatives, and aqueous soluble O-sulfonated bile acids are also included as soluble bile acid salts. Soluble bile acid may include an aqueous preparation of a free acid form of bile acid combined with one of HCl, acetic acid, ammonia, or arginine.

Bile acids used in this invention include, but are not limited to ursodeoxycholic acid, chenodeoxycholic acid, cholic acid, hyodeoxycholic acid, deoxycholic acid, 7-oxolithocholic acid, lithocholic acid, iododeoxycholic acid, iocholic acid, tauroursodeoxycholic acid, taurochenodeoxycholic acid, taurodeoxycholic acid, taurolithocholic acid, glycoursodeoxycholic acid, taurocholic acid, glycocholic acid, and their derivatives at a hydroxyl or carboxylic acid group on the steroid nucleus.

A major advantage of the instant invention is that by delivery of bile acid in solution, it achieves higher in vivo levels of bile acids than conventional preparations. Therefore, the therapeutic potential of bile acid may be more fully acheived than previous formulations. The in vivo levels of bile acids attainable with existing formulations in which bile is incompletely solubilized are lower and require administration of larger amounts of bile acids. Since bile acid is completely dissolved in the inventive formulations, higher in vivo levels of bile acid may be achieved, even though lower doses are administered.

In some embodiments of the invention, a plurality of bile acids are used in a single formulation. Mixtures of two or more bile salts of differing hydrophobic activity may behave as a single bile salt of an intermediate hydrophobic activity. As a result, detergent properties and the toxicity of mixtures of two bile acids of differing hydrophobic activity often are intermediate between the individual components.

Carbohydrates suitable for use in the invention include aqueous soluble starch conversion products and aqueous soluble non-starch polysaccharides. For purposes of the invention, aqueous soluble starch conversion products are defined as follows:
1. They may be obtained under various pH conditions from the partial or incomplete hydrolysis of starch.
2. Non-limiting examples include maltodextrin, dextrin, liquid glucose, corn syrup solid (dried powder of liquid glucose), soluble starch, and soluble starch, preferably maltodextrin or corn syrup solid, most preferably corn syrup solid. Particularly preferred are MALTRIN® M200, a corn syrup solid, and MALTRIN® M700 a maltodextrin, both of which are manufactured by GPC®, Grain Processing Corporation of Muscatine, Iowa. For the purpose of this invention, the term "corn syrup" includes both corn syrup and liquid glucose.
3. If polymeric, the polymer has at least one reducing end and at least one non-reducing end. The polymer may be linear or branched.
4. The molecular weight is from about 100 mass units to over $10^6$ mass units. High molecular weight aqueous soluble starch conversion products are those having a molecular weight over $10^5$.

For purposes of the invention, aqueous soluble non-starch polysaccharides are defined as follows:
1. They may be obtained under various pH conditions by various hydrolytic or synthetic mechanisms.
2. Non-limiting examples include to dextran, guar gum, pectin, indigestible soluble fiber.
3. If polymeric, the polymer has at least one reducing end and at least one non-reducing end. The polymer may be linear or branched.
4. The molecular weight is from about 100 mass units to over $10^6$ mass units. Preferably the molecular weight is over $10^5$ mass units.

The amount of high molecular weight aqueous soluble starch conversion product and/or soluble non-starch polysaccharide used in the invention is at least the amount needed to render the chosen bile acid salt soluble in the concentration desired and in the pH range desired. In preferred embodiments of the invention, the approximate minimal quantity of maltodextrin required to prevent the precipitation of bile acids from the aqueous solution dosage forms of the invention is 5 g for every 0.2 g of ursodeoxycholic acid, 25 g for every 1 g of ursodeoxycholic acid, and 50 g for every 2 g of ursodeoxycholic acid in 100 mL of water. In preferred embodiments of the invention, the approximate minimal quantity of maltodextrin is 30 g for every 200 mg of chenodeoxycholic acid, 12 g for every 200 mg of 7-ketolithocholic acid, 10 g for every 200 mg of cholic acid and 50 g for every 200 mg of deoxycholic acid. In preferred embodiments of the invention, the approximate minimal quantity of liquid glucose (commercial light corn syrup) required to prevent the precipitation of bile acids from the aqueous solution dosage forms of the invention is 80 g for every 500 mg ursodeoxycholic acid in 100 mL water, and 80 g for every 500 mg ursodeoxycholic acid in 200 mL water. In preferred embodiments of the invention, the approximate minimal quantity of dried powder of liquid glucose (corn syrup solid, e.g., MALTRIN® M200) required to prevent the precipitation of bile acids from the aqueous solution dosage forms of the invention is 30 g for every 500 mg ursodeoxycholic acid in 100 mL water, and approximately 30 g for every 500 mg of ursodeoxycholic acid in 200 mL water. In preferred embodiments of the invention, the approximate minimal quantity of soluble non-starch polysaccharide (e.g., pectin, guar gum, gum arabic) required to prevent the precipitation of bile acids from the aqueous solution dosage forms of the invention is 50 g guar gum for every 500 mg ursodeoxycholic acid in 100 mL water and 80g of pectin for every 500 mg of ursodeoxycholic acid in 100 mL water. The minimal required quantity of high molecular weight aqueous soluble starch conversion products or soluble non-starch polysaccharide is primarily determined by the absolute quantity of bile acids in the solution formulation rather than the concentration.

In some embodiments of the invention, a formulation may comprise cyclodextrin.

In some embodiments of the invention, the formulation further comprises dietary fiber. Non-limiting examples of dietary fiber include guar gum, pectin, psyllium, oat gum, soybean fiber, oat bran, corn bran, cellulose and wheat bran.

In some embodiments of the invention, the formulation further comprises emulsifying agents. For the purpose of the invention, the term "emulsifying agent" includes emulsifying agents and suspending agents. Non-limiting examples of emulsifying agents include guar gum, pectin, acacia, carrageenan, carboxymethyl cellulose sodium, hydroxymethyl cellulose, hydroxypropyl cellulose, methyl cellulose, polyvinyl alcohol, povidone, tragacanth gum, xanthan gum, and sorbitan ester.

The selected pH range for which the formulation will not precipitate its bile acid, starch conversion product, soluble non-starch polysaccharide or its pharmaceutical compound may be any range of pH levels obtainable with an aqueous system. Preferably this range is between about pH 1 and about pH 14 and more preferably between about pH 1 and about pH 10. Still more preferably the range is any subset of the range of pH levels obtainable in an aqueous system sufficient for the pharmaceutical formulation to remain in solution from preparation, to administration, to absorption in the body, according to the method of administration.

The invention contemplates the use of a broad range of pharmaceutical compounds. Non-limiting examples include hormones, hormone antagonists, analgesic, antipyretics, anti-inflammatory drugs, immunoactive drugs, antineoplastic drugs, antibiotics, anti-inflammatory agents, sympathomimetic drugs, anti-infective drugs, anti-tumor agents, and anesthetics. Further non-limiting examples include drugs that target or effect the gastrointestinal tract, liver, cardiovascular system, and respiratory system. Further non-limiting examples of pharmaceutical compounds include insulin, heparin, calcitonin, ampicillin, octreotide, sildenafil citrate, calcitriol, dihydrotachysterol, apomorphine, yohimbine, trazadone, acyclovir, amantadine.HCl, rimantadine.HCl, cidofovir, delavirdine.mesylate, didanosine, famciclovir, foscarnet sodium, fluorouracil, ganciclovir sodium, idoxuridine, interferon-α, lamivudine, nevirapine, penciclovir, ribavirin, stavudine, trifluridine, valacyclovir.HCl, zalcitabine, zidovudine, indinavir.$H_2SO_4$, ritonavir, nelfinavir.$CH_3SO_3H$, saquinavir.$CH_3SO_3H$, d-penicillamine, chloroquine, hydroxychloroquine, aurothioglucose, gold sodium thiomalate, auranofin levamisole, dacarbazine, isoprinosine, methyl inosine monophosphate, muramyl dipeptide, diazoxide, hydralazine.HCl, minoxidil, dipyridamole, isoxsuprine.HCl, niacin, nylidrin.HCl, phentolamine, doxazosin.$CH_3SO_3H$, prazosin.HCl, terazocin.HCl, clonidine.HCl, nifedipine, molsidomine, amiodarone, acetylsalicylic acid, verapamil, diltiazem, nisoldipine, isradipine, bepridil, isosorbide.dinitrate, pentaerythrytol.tetranitrate, nitroglycerin, cimetidine, famotidine, nizatidine, ranitidine, lansoprazole, omeprazole, misoprostol, sucralfate, metoclopramide.HCl, erythromycin, bismuth compound, alprostadil, albuterol, pirbuterol, terbutaline.$H_2SO_4$, salmetrol, aminophylline, dyphylline, ephedrine, ethylnorepinephrine, isoetharine, isoproterenol, metaproterenol, nedocromil, oxtriphylline, theophylline, bitolterol, fenoterol, budesonide, flunisolide, beclomethasone.dipropionate, fluticasone.propionate, codeine, codeine sulfate, codeine phosphate, dextromethorphan.HBr, triamcinolone.acetonide, montelukast sodium, zafirlukast, zileuton, cromolyn sodium, ipratropium bromide, nedocromil sodium benzonate, diphenhydramine.HCl, hydrocodone.bitartarate, methadone.HCl, morphine sulfate, acetylcysteine, guaifenesin, ammonium carbonate, ammonium chloride, antimony potassium tartarate, glycerin, terpin.hydrate, colfosceril palmitate, atorvastatin.calcium, cervastatin.sodium, fluvastatin.sodium, lovastatin, pravastatin.sodium, simvastatin, picrorrhazia kurroa, andographis paniculata, moringa oleifera, albizzia lebeck, adhatoda vasica, curcuma longa, momordica charantia, gymnema sylvestre, terminalia arjuna, azadirachta indica, tinosporia cordifolia, metronidazole, amphotericin B, clotrimazole, fluconazole, haloprogin, ketoconazole, griseofulvin, itraconazole, terbinafin.HCl, econazole.$HNO_3$, miconazole, nystatin, oxiconazole.$HNO_3$, sulconazole.$HNO_3$, cetirizine.2HCl, dexamethasone, hydrocortisone, prednisolone, cortisone, catechin and its derivatives, glycyrrhizin, glycyrrhizic acid, betamethasone, fludrocortisone.acetate, flunisolide, fluticasone.propionate, methyl prednisolone, somatostatin, lispro, glucagon, proinsulin, insoluble insulins, acarbose, chlorpropamide, glipizide, glyburide, metformin.HCl, repaglinide, tolbutamide, amino acid, colchicine, sulfinpyrazone, allopurinol, piroxicam, tolmetin sodium, indomethacin, ibuprofen, diflunisal, mefenamic acid, naproxen, and trientine.

Additional pharmaceutical compounds that may be included in the formulation are any compounds which remain soluble when added to the formulation. With an additional pharmaceutical compound in the formulation, a bile acid in solution may act as an adjuvant, carrier, or enhancer for the solubility of certain therapeutically active agents, including, but not limited to, insulin (pH 7.4–7.8), heparin (pH 5–7.5), calcitonin, ampicillin, amantadine, rimantadine, sildenafil, neomycin sulfate (pH 5–7.5), apomorphine, yohimbin, trazodone, ribavirin, paclitaxel and its derivatives, retinol, and tretinoin, which are soluble and stable in acid and/or alkali and can be added as needed into these aqueous solution dosage forms of certain concentrations of bile acids in this invention. Certain therapeutically active agents, including, but not limited to, metformin HCl (pH 5–7), ranitidine HCl, cimetidine, lamivudine, cetrizine 2HCl (pH 4–5), amantadine, rimantadine, sildenafil, apomorphine, yohimbine, trazodone, ribavirin and dexamethasone, hydrocortisone, prednisolone, triamcinolone, cortisone, niacin, taurine, vitamins, naturally occurring amino acids, catechin and its derivatives, glycyrrhizal extract and its main constituents such as glycyrrhizin and glycyrrhizic acid, water soluble bismuth compounds (e.g., bismuth sodium tartrate), and which are soluble and stable in acid and/or alkali can be added as needed into these aqueous solution dosage formulations containing ursodeoxycholic acid in this invention.

According to the invention bismuth compounds comprise an aqueous soluble reaction product between a bismuth ion and a chelator. Non-limiting examples of such chelators include citric acid, tartaric acid, malic acid, lactic acid and eidetic acid and alkalies. Non-limiting examples of bismuth compounds include an ammonium salt of a bismuth chelation complex, bismuth citrate, bismuth gallate, bismuth sulphate, bismuth subnitrate, bismuth subsalicylate, tripotassium dicitrato bismuthate, and bismuth sodium tartrate.

The invention contemplates the use of pH adjustable agents. Non-limiting examples include HCl, $H_2SO_4$, $HNO_3$, $CH_3COOH$, citric acid, malic acid, tartaric acid, lactic acid, phosphate, eidetic acid and alkalies.

In some embodiements of the invention, the formulations may be used to treat human and mammalian diseases. The invention contemplates treating gastrointestinal disorders, liver diseases, gall stones, and hyperlipidemia. Non-limiting examples of liver diseases include alcohol-induced liver diseases and non-alcohol-induced liver diseases. Non-limiting examples of gastrointestinal disorders include chronic gastritis, reflux gastritis, and peptic ulcer disease. Non-limiting examples of non-alcohol-induced liver diseases include primary biliary cirrhosis, acute and chronic hepatitis, primary sclerosing cholangitis, chronic active hepatitis, and excess accumulation of fat in the liver. The invention further contemplates treating viral, bacterial and fungal diseases. In some embodiments of the invention, a formulation is administered to treat and/or erradicate *Helicobacter pylori* infection. In some embodiments of the invention, a formulation is administered to treat and/or erradicate hepatitis C virus infection, influenza A, Influenza C, parainfluenza 1, sendai, rubella, and pseudorabies virus. In some embodiments of the invention, a formulation is administered to treat acute or chronic inflammatory diseases. Non-limiting examples of inflammatory diseases include bronchitis, chronic pharyngitis, and chronic tonsillitis. In some embodiments of the invention, a formulation is administered to treat hypercholersterolemia.

In some embodiments of the invention, the formulation is modified such that it may be administered as a liquid, solid, powder or tablet. In some embodiments of the invention, the formulation is comprised in a syrup, thick syrup or paste. A non-limiting example of a syrup is a solution of maltodextrin wherein the concentration of maltodextrin is less than 1.0 kg/L. A non-limiting example of a thick syrup is a solution of maltodextrin wherein the concentration of maltodextrin is between 1.0 kg/L and 1.2 kg/L inclusive. A non-limiting example of a paste is a solution of maltodextrin wherein the concentration of maltodextrin is greater than 1.2 kg/L.

EXAMPLES

The stability of dosage formulations of the invention were evaluated by measuring the concentration of the relevant bile acid over time in preparations comprising soluble bile acid, a high molecular weight aqueous soluble starch conversion product, and water at various pH and temperature levels. The retention time of each bile acid may be adjusted as needed to permit individual analysis each bile acid present in a complex samples, i.e. a sample having a plurality of bile acids.

The stability tests were conducted on three different aqueous solution systems:

1. A bile acid and a high molecular weight aqueous soluble starch conversion product were combined in aqueous solution according to Example I, with results as shown in Tables 1A and 1B.
2. Mixed bile acids and high molecular weight aqueous soluble starch conversion products were combined in aqueous solution according to Example II, with results as shown in Table 2.
3. Bile acids, high molecular weight aqueous soluble starch conversion products and branched chained amino acids (e.g. leucine, isoleucine, valine, or other amino acid with a branched side chain) were combined in aqueous solution according to Example IV, with results as shown in Tables 3A through 3F.

The stability tests were performed with HPLC and microscope light at various pH conditions under the normal and accelerated conditions. Accelerated conditions for testing pharmaceutical compositions have been described (Remington, *The Science and Practice of Pharmacy*, 19th ed., p. 640). All of these stability test results were satisfactory in that the concentration of bile acid as measured by HPLC did not change appreciably over time at various pH levels. Thus, the formulations of the examples are suitable for preparing a commercial liquid dosage form. Particularly, all solution formulations which contained bile acid showed excellent results in the stability tests with no precipitation and no physical appearance changes over the test period. Some formulations remain stable for over 2 years.

Moreover, the solution stability tests were conducted on the aqueous solution dosage forms comprising the mixture of aqueous soluble UDCA, branched chained amino acid (leucine, isoleucine, valine) and maltodextrin according to example IV as a typical example of the solution dosage forms in which bile acid as a therapeutically active agent, as an adjuvant or carrier, pharmaceutically active agent, or enhancer of solubility, and high molecular weight aqueous soluble starch conversion products or soluble non-starch polysaccharides are dissolved. According to the test results, there is no discoloration, no clarity changes, and no precipitation. Furthermore, there are no detectable impurities from the deterioration of UDCA or branched chained amino acids when examined by HPLC at various pH conditions such as pH 1, 3, 5, 7, 9, and 10 under the accelerated conditions or incubation at (50° C.).

The aqueous solution dosage forms according to this invention did not change either physically or chemically at various pH conditions under the accelerated conditions despite the addition of therapeutically and chemically active agents that are stable and soluble in hydrochloric acid solution. Therefore, these aqueous solution systems are extremely valuable pharmaceutical dosage forms for the therapeutically active bile acids preparations, and/or the drug (pharmaceutical compound) delivery preparations in which bile acids play roles as the adjuvant of drug, the carrier of drug, or the enhancer of solubility of a drug by micelle formation at various pH conditions without the stability problems, including precipitation in acidic conditions.

For the solution stability test for each bile acid, HPLC was used to measure the concentration of the relevant soluble bile acid under the following conditions: the elution solvent of 0.02 M $KH_2PO_4$:acetonitrile in a ratio of 55:45, with a pH of 3.01, the flow rate was 0.8 mL/min., the injection volume was 20 μL, wave length for detection was 195 nm. In the tables, the concentration of the indicated bile acid salt for each of the three numbered trials and the average thereof is reported on each line. The percentage indicates the relative concentration of the bile acid salt after incubation for a certain amount of time in comparison with the initial concentration.

Example I

Solution dosage forms that were prepared according to the following guidelines did not show any precipitation at any pH tested.

| | |
|---|---|
| Soluble bile acid | 200 mg (as free acid) |
| Minimal quantity of maltodextrin | for CDCA: approx. 30 g; |
| | for UDCA: approx. 5 g; |
| | for 7-ketolithocholic acid: approx. 12 g; |
| | for cholic acid: approx. 10 g; |
| | for deoxycholic acid: approx. 50 g; |
| | for hyodeoxycholic acid: approx. 3.5 g |
| Purified water to make | 100 mL |

100 mL of the aqueous solution in which one of the above bile acids is dissolved was prepared. Into the resulting clear solution, maltodextrin, a high molecular weight aqueous soluble starch conversion product, was added with agitation at room temperature. Purified water was added to adjust the total volume to be 100 mL. According to the instant invention and all examples, purified water is deionized, distilled deionized-distilled water, or a grade commonly used for pharmaceutical preparations.

Based on these formulas, the aqueous solution dosage forms of various concentrations of certain bile acids (or salts) with its corresponding minimal quantity or more of high molecular weight aqueous soluble starch conversion products (for example; maltodextrin, liquid glucose, dried powder of liquid glucose (commercial corn syrup solid), dextran, dextrin, and soluble starch) or soluble non-starch polysaccharide (e.g. guar gum, pectin, gum arabic) were prepared.

Example II

Solution dosage forms that were prepared according to the following guidelines did not show any precipitation at any pH tested.

| | |
|---|---|
| Soluble cholic acid | 200 mg (as free acid), |
| Soluble 7-ketolithocholic acid | 200 mg (as free acid), |
| Soluble chenodeoxycholic acid | 200 mg (as free acid), |
| Minimal quantity of maltodextrin | 40 g, and |
| Purified water to make | 100 mL |

60 mL of the aqueous solution in which soluble cholic acid, soluble 7-ketolithocholic acid, and soluble chenodeoxycholic acid are dissolved, was prepared. Into the resulting clear solution, maltodextrin was added with agitating at room temperature. Purified water was added to adjust the total volume to be 100 mL.

Using this formulation, the stability test for the aqueous solution of the mixture of various bile acids which can control the hydrophillicity or hydrophobicity was conducted.

Table 1A shows the results of a test of stability over time at pH 7 and 50° C. of formulations of CA, 7-ketolithocholic acid, CDCA and DCA in solution with maltodextrin prepared according to Example I. The concentrations of the bile acids were measured by HPLC and the concentration of the bile acid as a percentage of its concentration on day 0 is reported in the column labeled percentage.

Table 1B shows the results of the test of stability over time at pH 10 and 50° C. of formulations of CA, 7-ketolithocholic acid, CDCA and DCA in solution with maltodextrin prepared according to Example I.

Table 2 shows results of the test of stability over time at pH 1 and 50° C. of formulations of CA, 7-ketolithocholic acid, CDCA and DCA in solution with maltodextrin at pH 1 and 50° C. prepared according to Example II.

TABLE 1A

| Day | #1 | #2 | #3 | Average | Percentage |
|---|---|---|---|---|---|
| CA | | | | | |
| 0 | 0.529 | 0.530 | 0.522 | 0.527 | 100.0 |
| 4 | 0.460 | 0.524 | 0.524 | 0.502 | 95.4 |
| 7 | 0.520 | 0.525 | 0.547 | 0.531 | 100.8 |
| 20 | 0.516 | 0.576 | 0.535 | 0.542 | 103.0 |
| KLCA | | | | | |
| 0 | 0.888 | 0.879 | 0.874 | 0.880 | 100.0 |
| 4 | 0.871 | 0.887 | 0.888 | 0.882 | 100.2 |
| 7 | 0.897 | 0.893 | 0.888 | 0.893 | 101.4 |
| 20 | 0.893 | 0.909 | 0.894 | 0.899 | 102.1 |
| CDCA | | | | | |
| 0 | 0.572 | 0.539 | 0.530 | 0.547 | 100.0 |
| 4 | 0.540 | 0.552 | 0.576 | 0.556 | 101.6 |
| 7 | 0.581 | 0.588 | 0.553 | 0.574 | 105.0 |
| 20 | 0.565 | 0.608 | 0.560 | 0.578 | 105.7 |
| DCA | | | | | |
| 0 | 0.499 | 0.491 | 0.489 | 0.493 | 100.0 |
| 4 | 0.501 | 0.500 | 0.474 | 0.491 | 99.6 |
| 7 | 0.488 | 0.487 | 0.484 | 0.486 | 98.6 |
| 20 | 0.478 | 0.476 | 0.472 | 0.475 | 96.3 |

TABLE 1B

| Day | #1 | #2 | #3 | Average | Percentage |
|---|---|---|---|---|---|
| CA | | | | | |
| 0 | 0.534 | 0.524 | 0.490 | 0.516 | 100.0 |
| 4 | 0.501 | 0.509 | 0.524 | 0.511 | 99.1 |
| 7 | 0.552 | 0.518 | 0.533 | 0.534 | 103.6 |
| 20 | 0.535 | 0.563 | 0.548 | 0.549 | 106.4 |
| KLCA | | | | | |
| 0 | 0.879 | 0.874 | 0.857 | 0.870 | 100.0 |
| 4 | 0.870 | 0.873 | 0.880 | 0.874 | 100.5 |
| 7 | 0.893 | 0.876 | 0.882 | 0.884 | 101.5 |
| 20 | 0.887 | 0.893 | 0.887 | 0.889 | 102.2 |
| CDCA | | | | | |
| 0 | 0.541 | 0.532 | 0.495 | 0.522 | 100.0 |
| 4 | 0.511 | 0.519 | 0.538 | 0.523 | 100.0 |
| 7 | 0.564 | 0.527 | 0.540 | 0.544 | 104.1 |
| 20 | 0.556 | 0.569 | 0.558 | 0.561 | 107.4 |
| DCA | | | | | |
| 0 | 0.491 | 0.488 | 0.471 | 0.483 | 100.0 |
| 4 | 0.493 | 0.487 | 0.472 | 0.484 | 100.2 |
| 7 | 0.479 | 0.488 | 0.479 | 0.482 | 99.7 |
| 20 | 0.468 | 0.478 | 0.479 | 0.475 | 98.3 |

TABLE 2

| Day | #1 | #2 | #3 | Average | Percentage |
|---|---|---|---|---|---|
| CA | | | | | |
| 0 | 0.516 | 0.509 | 0.503 | 0.509 | 100.0 |
| 4 | 0.453 | 0.453 | 0.466 | 0.457 | 89.8 |
| 7 | 0.434 | 0.426 | 0.468 | 0.443 | 86.9 |
| 20 | 0.207 | — | 0.206 | 0.207 | 40.6 |
| KLCA | | | | | |
| 0 | 0.883 | 0.877 | 0.869 | 0.876 | 100.0 |
| 4 | 0.870 | 0.866 | 0.847 | 0.861 | 98.3 |
| 7 | 0.848 | 0.844 | 0.843 | 0.845 | 96.4 |
| 20 | 0.661 | — | 0.651 | 0.656 | 74.9 |
| CDCA | | | | | |
| 0 | 0.560 | 0.528 | 0.513 | 0.534 | 100.0 |
| 4 | 0.488 | 0.510 | 0.519 | 0.506 | 94.7 |
| 7 | 0.460 | 0.469 | 0.463 | 0.464 | 87.0 |
| 20 | 0.169 | — | 0.154 | 0.161 | 30.2 |

Example III

Solution dosage forms that were prepared according to the following guidelines did not show any precipitation at any pH tested.

| | |
|---|---|
| Soluble UDCA | 200 mg (100 mg–2000 mg as free base) |
| Minimal quantity of maltodextrin | approx. 5 g (approx. 1.25 g–50 g) |
| Preservatives | q.s. |
| Flavoring agent | q.s. |
| Sweetener | q.s. |
| Purified water to | 100 mL |

80 mL of an aqueous solution in which soluble UDCA is dissolved was prepared, and then, maltodextrin was added into the clear solution with agitating at room temperature. Into the resulting clear solution, sweetener, preservatives and flavoring agents were added in quantities suitable for a pharmaceutical formulation. Purified water was added to adjust the total volume to be 100 mL.

In these formulas, the aqueous solution dosage forms of various concentrations of ursodeoxycholic acid (or its salts) with its corresponding minimal quantity or more of aqueous soluble starch conversion products (for example, maltodextrin, liquid glucose, dried powder of liquid glucose (commercial corn syrup solid), dextran, or soluble starch).

Figure 6:
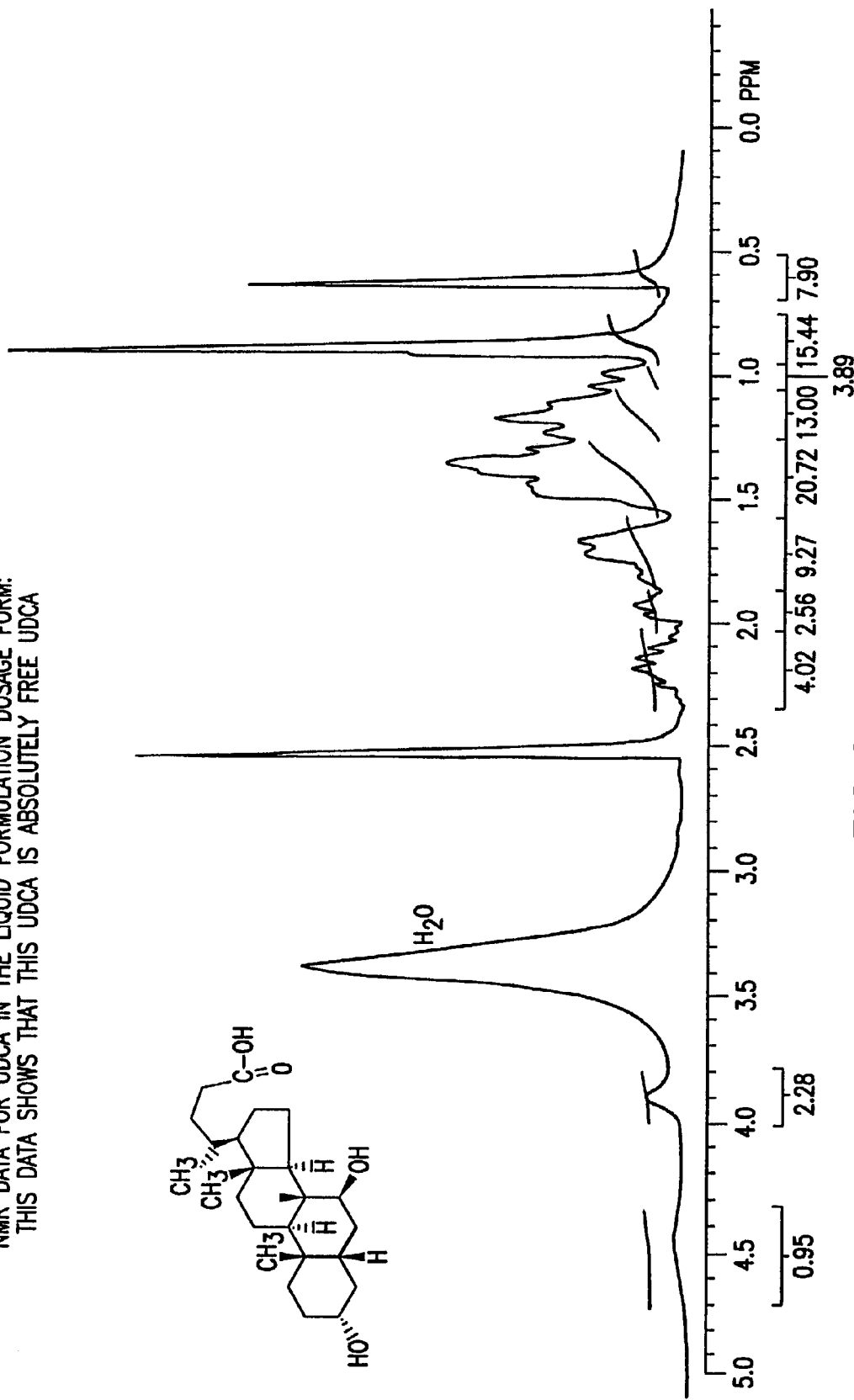
FIG. 6: NMR data for UDCA in a liquid formulation dosage form prepared according to Example III without preservatives, flavoring agent, and sweetener.

FIG. 6 is an NMR spectrum of UDCA illustrating that UDCA, when in a composition prepared according to Example III, is absolutely free UDCA. That is, the carboxylic acid of UDCA at C-24 is the free form (R—COOH) and two hydroxy group at C-3 and C-7 are in the free form (R—OH)

Figure 7:
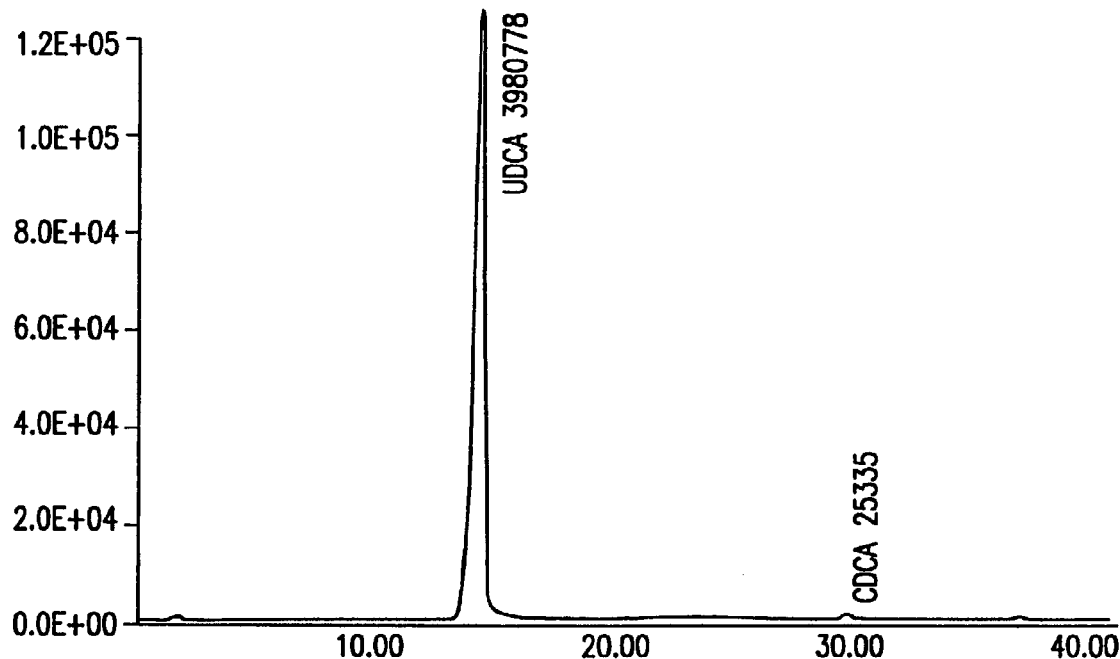
FIG. 7: HPLC trace of UDCA in a liquid formulation dosage form prepared according to Example III without preservatives, flavoring agent, and sweetener.
Figure 8:
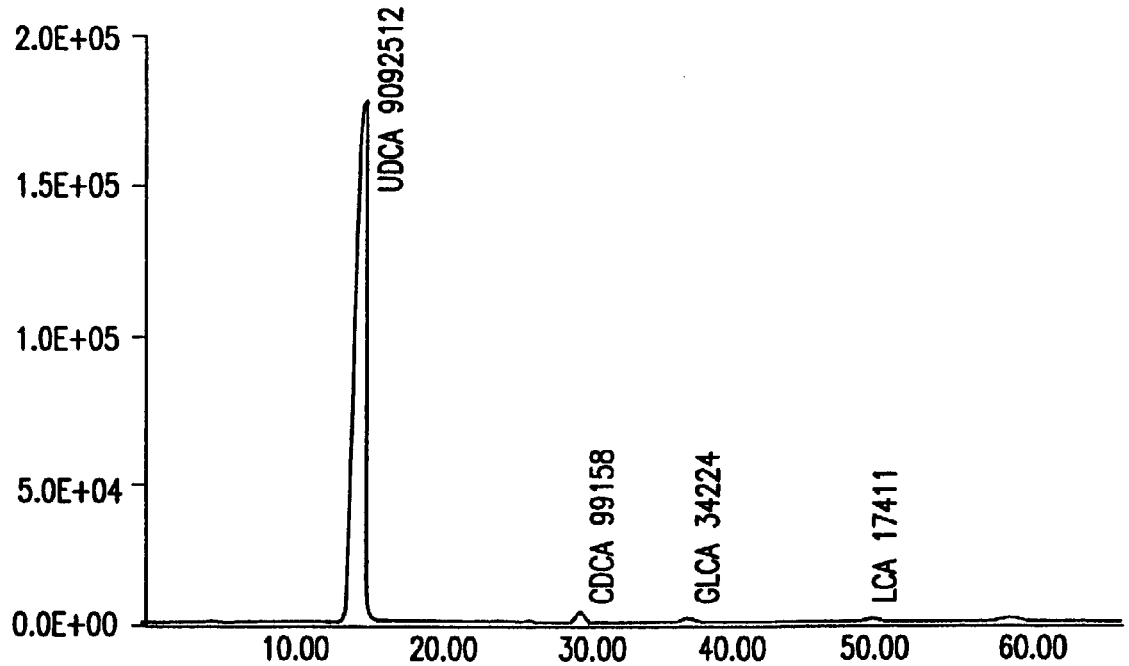
FIG. 8: HPLC trace of a UDCA standard.

In addition, the HPLC profile of UDCA in a composition prepared according to Example III (FIG. 7) is similar to the profile of of UDCA dissolved in methanol (FIG. 8). This data shows that there is no UDCA-complex compound. There is only free UDCA. The UDCA standard solution was prepared by dissolving 100 mg UDCA in 100 mL of methanol. A mixture of acetonitrile (51), water (49), and acetic acid (1) was used as the mobile phase.

Example IV

Solution dosage forms that were prepared according to the following guidelines did not show any precipitation at any pH within the selected, desired range of pH values.

| | |
|---|---|
| Soluble UDCA | 0.2 g (1 g–2 g as free acid) |
| Maltodextrin | 5 g (35 g–50 g) |
| Branched chained amino acid (e.g. leucine, isoleucine, valine) | 15 g (5 g–15 g as free base) |
| Sweetener | q.s. |
| Flavoring agent | q.s. |
| Purified water to | 100 mL |

85 mL of the aqueous solution in which soluble UDCA is dissolved was prepared, and then maltodextrin was added into the clear solution. Into the resulting clear solution, branched amino acids were added with adjusting the pH (4–7) with agitation and then sweetener, preservatives, and flavoring agent were added. Purified water was added to adjust the total volume to be 100 mL.

Based on these formulations, the aqueous solution dosage forms of various concentrations of ursodeoxycholic acid (or its salt) and its corresponding minimal quantity or more of maltodextrin, liquid glucose, dried powder of liquid glucose (commercial corn syrup) or dextran) with various quantities of branched amino acid (total amount of leucine, isoleucine and valine) were prepared.

Tables 3A to 3F show stability test results over time of formulation prepared with amino acids according to Example IV. All stability tests were conducted at 50° C. Stability test results at pH 1 (Table 3A), pH 3 (Table 3B), pH 5 (Table 3C), pH 7 (Table 3D), pH 9 (Table 3E), and pH 10 (Table 3F) are shown.

TABLE 3A

Stability of UDCA solution according to Example IV at pH1, 50° C.

| Day | #1 | #2 | #3 | Average | Percentage |
|---|---|---|---|---|---|
| Ile | | | | | |
| 0 | 0.261 | 0.236 | 0.249 | 0.248 | 100.0 |
| 1 | 0.256 | 0.275 | 0.251 | 0.261 | 105.0 |
| 2 | 0.268 | 0.263 | 0.251 | 0.260 | 104.9 |

TABLE 3A-continued

Stability of UDCA solution according to Example IV at pH1, 50° C.

| Day | #1 | #2 | #3 | Average | Percentage |
|---|---|---|---|---|---|
| 6 | 0.295 | 0.268 | 0.291 | 0.285 | 114.6 |
| 7 | 0.249 | 0.254 | 0.267 | 0.257 | 103.4 |
| 8 | 0.253 | 0.243 | 0.240 | 0.245 | 98.8 |
| 9 | 0.263 | 0.268 | 0.263 | 0.265 | 106.6 |
| Leu | | | | | |
| 0 | 0.485 | 0.428 | 0.470 | 0.461 | 100.0 |
| 1 | 0.470 | 0.477 | 0.456 | 0.468 | 101.5 |
| 2 | 0.485 | 0.481 | 0.460 | 0.475 | 103.1 |
| 6 | 0.553 | 0.510 | 0.529 | 0.531 | 115.1 |
| 7 | 0.478 | 0.473 | 0.513 | 0.488 | 105.8 |
| 8 | 0.474 | 0.454 | 0.511 | 0.480 | 104.0 |
| 9 | 0.483 | 0.485 | 0.476 | 0.481 | 104.4 |
| Val | | | | | |
| 0 | 0.506 | 0.448 | 0.460 | 0.471 | 100.0 |
| 1 | 0.438 | 0.458 | 0.471 | 0.456 | 96.7 |
| 2 | 0.479 | 0.485 | 0.513 | 0.492 | 104.5 |
| 6 | 0.505 | 0.536 | 0.549 | 0.530 | 112.4 |
| 7 | 0.494 | 0.465 | 0.496 | 0.485 | 102.9 |
| 8 | 0.488 | 0.491 | 0.459 | 0.479 | 101.7 |
| 9 | 0.479 | 0.496 | 0.490 | 0.488 | 103.6 |
| Sol | | | | | |
| 0 | 0.319 | 0.315 | 0.322 | 0.319 | 100.0 |
| 1 | 0.332 | 0.344 | 0.351 | 0.342 | 107.4 |
| 2 | 0.371 | 0.339 | 0.403 | 0.371 | 116.4 |
| 6 | 0.396 | 0.409 | 0.411 | 0.405 | 127.2 |
| 7 | 0.365 | 0.351 | 0.381 | 0.366 | 114.7 |
| 8 | 0.409 | 0.365 | 0.331 | 0.368 | 115.6 |
| 9 | 0.338 | 0.391 | 0.374 | 0.368 | 115.4 |
| UDCA | | | | | |
| 0 | 0.388 | 0.387 | 0.389 | 0.388 | 100.0 |
| 1 | 0.367 | 0.370 | 0.366 | 0.368 | 94.8 |
| 2 | 0.374 | 0.388 | 0.388 | 0.383 | 98.9 |
| 6 | 0.371 | 0.380 | 0.382 | 0.377 | 97.3 |
| 7 | 0.378 | 0.376 | 0.379 | 0.378 | 97.4 |
| 8 | 0.374 | 0.382 | 0.384 | 0.380 | 97.9 |
| 9 | 0.370 | 0.367 | 0.370 | 0.369 | 95.1 |

TABLE 3B

Stability of UDCA solution according to Example IV at pH 3, 50° C.

| Day | #1 | #2 | #3 | Average | Percentage |
|---|---|---|---|---|---|
| Ile | | | | | |
| 0 | 0.261 | 0.254 | 0.253 | 0.256 | 100.0 |
| 1 | 0.266 | 0.268 | 0.261 | 0.265 | 103.3 |
| 2 | 0.273 | 0.243 | 0.247 | 0.254 | 99.3 |
| 6 | 0.296 | 0.306 | 0.300 | 0.301 | 117.4 |
| 7 | 0.247 | 0.265 | 0.257 | 0.256 | 100.0 |
| 8 | 0.250 | 0.247 | 0.247 | 0.248 | 96.7 |
| 13 | 0.285 | 0.240 | 0.250 | 0.258 | 100.9 |
| Leu | | | | | |
| 0 | 0.495 | 0.465 | 0.452 | 0.471 | 100.0 |
| 1 | 0.489 | 0.480 | 0.470 | 0.480 | 101.9 |
| 2 | 0.495 | 0.472 | 0.481 | 0.483 | 102.6 |
| 6 | 0.522 | 0.532 | 0.556 | 0.537 | 114.0 |
| 7 | 0.492 | 0.482 | 0.491 | 0.488 | 103.7 |
| 8 | 0.543 | 0.515 | 0.495 | 0.517 | 109.9 |
| 13 | 0.512 | 0.496 | 0.543 | 0.517 | 109.8 |
| Val | | | | | |
| 0 | 0.485 | 0.491 | 0.498 | 0.491 | 100.0 |
| 1 | 0.467 | 0.481 | 0.446 | 0.465 | 94.6 |
| 2 | 0.510 | 0.493 | 0.527 | 0.510 | 103.8 |
| 6 | 0.527 | 0.491 | 0.553 | 0.524 | 106.6 |

TABLE 3B-continued

Stability of UDCA solution according to Example IV at pH 3, 50° C.

| Day | #1 | #2 | #3 | Average | Percentage |
|---|---|---|---|---|---|
| 7 | 0.485 | 0.481 | 0.468 | 0.478 | 97.3 |
| 8 | 0.490 | 0.491 | 0.544 | 0.508 | 103.5 |
| 13 | 0.519 | 0.498 | 0.517 | 0.511 | 104.1 |
| Sol | | | | | |
| 0 | 0.343 | 0.355 | 0.370 | 0.356 | 100.0 |
| 1 | 0.340 | 0.350 | 0.316 | 0.335 | 94.2 |
| 2 | 0.383 | 0.371 | 0.400 | 0.385 | 108.0 |
| 6 | 0.378 | 0.341 | 0.416 | 0.378 | 106.3 |
| 7 | 0.355 | 0.381 | 0.315 | 0.350 | 98.4 |
| 8 | 0.343 | 0.350 | 0.395 | 0.363 | 101.9 |
| 13 | 0.377 | 0.382 | 0.423 | 0.394 | 110.7 |
| UDCA | | | | | |
| 0 | 0.395 | 0.396 | 0.393 | 0.395 | 100.0 |
| 1 | 0.396 | 0.401 | 0.392 | 0.396 | 100.4 |
| 2 | 0.427 | 0.421 | 0.416 | 0.421 | 106.8 |
| 6 | 0.407 | 0.408 | 0.402 | 0.405 | 102.7 |
| 7 | 0.412 | 0.409 | 0.411 | 0.411 | 104.1 |
| 8 | 0.415 | 0.418 | 0.408 | 0.414 | 104.9 |
| 13 | 0.415 | 0.412 | 0.416 | 0.414 | 105.0 |

TABLE 3C

Stability of UDCA solution according to Example IV at pH 5, 50° C.

| Day | #1 | #2 | #3 | Average | Percentage |
|---|---|---|---|---|---|
| Ile | | | | | |
| 0 | 0.285 | 0.258 | 0.295 | 0.279 | 100.0 |
| 3 | 0.280 | 0.275 | 0.275 | 0.277 | 99.0 |
| 6 | 0.285 | 0.273 | 0.270 | 0.276 | 98.7 |
| 10 | 0.274 | 0.276 | 0.276 | 0.275 | 98.4 |
| 13 | 0.273 | 0.287 | 0.278 | 0.279 | 100.0 |
| 17 | 0.278 | 0.276 | 0.270 | 0.275 | 98.3 |
| 20 | 0.261 | 0.275 | 0.261 | 0.266 | 95.0 |
| 24 | 0.267 | 0.274 | 0.292 | 0.277 | 99.3 |
| Leu | | | | | |
| 0 | 0.495 | 0.467 | 0.535 | 0.499 | 100.0 |
| 3 | 0.510 | 0.495 | 0.494 | 0.500 | 100.1 |
| 6 | 0.489 | 0.479 | 0.484 | 0.484 | 97.0 |
| 10 | 0.486 | 0.490 | 0.499 | 0.492 | 98.5 |
| 13 | 0.492 | 0.509 | 0.508 | 0.503 | 100.8 |
| 17 | 0.514 | 0.508 | 0.504 | 0.509 | 100.9 |
| 20 | 0.499 | 0.500 | 0.499 | 0.499 | 101.1 |
| 24 | 0.488 | 0.509 | 0.528 | 0.508 | 101.9 |
| Val | | | | | |
| 0 | 0.483 | 0.498 | 0.481 | 0.487 | 100.0 |
| 3 | 0.492 | 0.494 | 0.526 | 0.504 | 103.4 |
| 6 | 0.459 | 0.475 | 0.481 | 0.472 | 96.8 |
| 10 | 0.500 | 0.436 | 0.480 | 0.472 | 96.9 |
| 13 | 0.464 | 0.451 | 0.474 | 0.463 | 95.0 |
| 17 | 0.407 | 0.491 | 0.462 | 0.453 | 93.0 |
| 20 | 0.471 | 0.512 | 0.477 | 0.487 | 99.9 |
| 24 | 0.471 | 0.476 | 0.458 | 0.468 | 96.1 |
| Sol | | | | | |
| 0 | 0.341 | 0.351 | 0.360 | 0.351 | 100.0 |
| 3 | 0.342 | 0.386 | 0.371 | 0.366 | 104.5 |
| 6 | 0.316 | 0.321 | 0.342 | 0.326 | 93.1 |
| 10 | 0.341 | 0.299 | 0.335 | 0.325 | 92.7 |
| 13 | 0.355 | 0.326 | 0.350 | 0.344 | 98.0 |
| 17 | 0.334 | 0.376 | 0.353 | 0.354 | 101.0 |
| 20 | 0.347 | 0.398 | 0.394 | 0.380 | 108.3 |
| 24 | 0.416 | 0.353 | 0.378 | 0.382 | 109.0 |
| UDCA | | | | | |
| 0 | 0.407 | 0.404 | 0.404 | 0.405 | 100.0 |
| 3 | 0.409 | 0.402 | 0.403 | 0.405 | 99.9 |

TABLE 3C-continued

Stability of UDCA solution according to Example IV at pH 5, 50° C.

| Day | #1 | #2 | #3 | Average | Percentage |
|---|---|---|---|---|---|
| 6 | 0.410 | 0.403 | 0.409 | 0.407 | 100.6 |
| 10 | 0.404 | 0.405 | 0.407 | 0.405 | 100.1 |
| 13 | 0.408 | 0.403 | 0.395 | 0.402 | 99.3 |
| 17 | 0.411 | 0.402 | 0.404 | 0.406 | 100.2 |
| 20 | 0.405 | 0.394 | 0.396 | 0.398 | 98.4 |
| 24 | 0.399 | 0.408 | 0.406 | 0.404 | 99.9 |

TABLE 3D

Stability of UDCA solution according to Example IV at pH 7, 50° C.

| Day | #1 | #2 | #3 | Average | Percentage |
|---|---|---|---|---|---|
| Ile | | | | | |
| 0 | 0.296 | 0.289 | 0.281 | 0.289 | 100.0 |
| 5 | 0.300 | 0.282 | 0.281 | 0.288 | 99.7 |
| 8 | 0.277 | 0.282 | 0.268 | 0.276 | 95.5 |
| 12 | 0.273 | 0.278 | 0.278 | 0.277 | 95.8 |
| 15 | 0.271 | 0.273 | 0.266 | 0.270 | 93.5 |
| 19 | 0.294 | 0.285 | 0.281 | 0.287 | 99.3 |
| Leu | | | | | |
| 0 | 0.519 | 0.513 | 0.495 | 0.509 | 100.0 |
| 5 | 0.499 | 0.499 | 0.498 | 0.498 | 97.9 |
| 8 | 0.498 | 0.513 | 0.480 | 0.497 | 97.7 |
| 12 | 0.508 | 0.516 | 0.515 | 0.513 | 100.9 |
| 15 | 0.503 | 0.505 | 0.499 | 0.502 | 98.7 |
| 19 | 0.521 | 0.509 | 0.516 | 0.515 | 101.3 |
| Val | | | | | |
| 0 | 0.483 | 0.530 | 0.525 | 0.513 | 100.0 |
| 5 | 0.502 | 0.447 | 0.499 | 0.483 | 94.1 |
| 8 | 0.488 | 0.498 | 0.493 | 0.493 | 96.2 |
| 12 | 0.490 | 0.469 | 0.443 | 0.467 | 91.2 |
| 15 | 0.492 | 0.541 | 0.442 | 0.492 | 95.9 |
| 19 | 0.458 | 0.500 | 0.482 | 0.480 | 93.6 |
| Sol | | | | | |
| 0 | 0.333 | 0.352 | 0.363 | 0.349 | 100.0 |
| 5 | 0.344 | 0.309 | 0.349 | 0.334 | 95.6 |
| 8 | 0.334 | 0.379 | 0.377 | 0.363 | 104.0 |
| 12 | 0.345 | 0.344 | 0.317 | 0.335 | 96.0 |
| 15 | 0.286 | 0.406 | 0.321 | 0.338 | 96.7 |
| 19 | 0.338 | 0.416 | 0.351 | 0.368 | 105.4 |
| UDCA | | | | | |
| 0 | 0.427 | 0.416 | 0.428 | 0.424 | 100.0 |
| 5 | 0.406 | 0.427 | 0.432 | 0.422 | 99.4 |
| 8 | 0.419 | 0.408 | 0.417 | 0.414 | 97.7 |
| 12 | 0.414 | 0.418 | 0.419 | 0.417 | 98.4 |
| 15 | 0.413 | 0.418 | 0.409 | 0.414 | 97.5 |
| 19 | 0.429 | 0.421 | 0.424 | 0.425 | 100.1 |

TABLE 3E

Stability of UDCA solution according to Example IV at pH 9, 50° C.

| Day | #1 | #2 | #3 | Average | Percentage |
|---|---|---|---|---|---|
| Ile | | | | | |
| 0 | 0.291 | 0.286 | 0.282 | 0.286 | 100.0 |
| 3 | 0.266 | 0.273 | 0.282 | 0.273 | 95.6 |
| 6 | 0.277 | 0.274 | 0.272 | 0.274 | 95.9 |
| 10 | 0.243 | 0.245 | 0.295 | 0.261 | 91.2 |
| 13 | 0.246 | 0.269 | 0.236 | 0.250 | 87.4 |
| 17 | 0.275 | 0.280 | 0.245 | 0.267 | 93.1 |

TABLE 3E-continued

Stability of UDCA solution according to Example IV at pH 9, 50° C.

| Day | #1 | #2 | #3 | Average | Percentage |
|---|---|---|---|---|---|
| Leu | | | | | |
| 0 | 0.509 | 0.513 | 0.511 | 0.511 | 100.0 |
| 3 | 0.485 | 0.487 | 0.492 | 0.488 | 95.5 |
| 6 | 0.495 | 0.496 | 0.492 | 0.494 | 96.8 |
| 10 | 0.470 | 0.467 | 0.528 | 0.488 | 95.6 |
| 13 | 0.461 | 0.491 | 0.450 | 0.467 | 91.5 |
| 17 | 0.468 | 0.516 | 0.500 | 0.495 | 96.9 |
| Val | | | | | |
| 0 | 0.508 | 0.476 | 0.484 | 0.489 | 100.0 |
| 3 | 0.463 | 0.487 | 0.485 | 0.478 | 97.8 |
| 6 | 0.493 | 0.473 | 0.495 | 0.487 | 99.5 |
| 10 | 0.441 | 0.428 | 0.471 | 0.447 | 91.3 |
| 13 | 0.467 | 0.483 | 0.537 | 0.496 | 101.3 |
| 17 | 0.499 | 0.495 | 0.501 | 0.498 | 101.8 |
| Sol | | | | | |
| 0 | 0.341 | 0.316 | 0.328 | 0.328 | 100.0 |
| 3 | 0.297 | 0.317 | 0.317 | 0.310 | 94.5 |
| 6 | 0.313 | 0.291 | 0.314 | 0.306 | 93.2 |
| 10 | 0.268 | 0.253 | 0.324 | 0.282 | 85.8 |
| 13 | 0.270 | 0.266 | 0.334 | 0.290 | 88.3 |
| 17 | 0.337 | 0.329 | 0.317 | 0.328 | 99.8 |
| UDCA | | | | | |
| 0 | 0.389 | 0.385 | 0.389 | 0.388 | 100.0 |
| 3 | 0.405 | 0.400 | 0.394 | 0.400 | 103.2 |
| 6 | 0.427 | 0.411 | 0.416 | 0.418 | 107.9 |
| 10 | 0.420 | 0.418 | 0.450 | 0.429 | 110.8 |
| 13 | 0.465 | 0.434 | 0.441 | 0.447 | 115.3 |
| 17 | 0.454 | 0.457 | 0.413 | 0.441 | 113.9 |

TABLE 3F

Stability of UDCA solution according to Example IV at pH 10, 50° C.

| Day | #1 | #2 | #3 | Average | Percentage |
|---|---|---|---|---|---|
| Ile | | | | | |
| 0 | 0.292 | 0.282 | 0.287 | 0.287 | 100.0 |
| 2 | 0.253 | 0.237 | 0.239 | 0.243 | 84.7 |
| 5 | 0.221 | 0.212 | 0.221 | 0.218 | 76.0 |
| 7 | 0.219 | 0.215 | 0.207 | 0.214 | 74.5 |
| 9 | 0.206 | 0.192 | 0.207 | 0.202 | 70.2 |
| Leu | | | | | |
| 0 | 0.507 | 0.495 | 0.509 | 0.504 | 100.0 |
| 2 | 0.462 | 0.442 | 0.442 | 0.449 | 89.1 |
| 5 | 0.429 | 0.428 | 0.427 | 0.428 | 85.0 |
| 7 | 0.410 | 0.417 | 0.414 | 0.414 | 82.1 |
| 9 | 0.417 | 0.377 | 0.418 | 0.404 | 80.2 |
| Val | | | | | |
| 0 | 0.480 | 0.506 | 0.471 | 0.486 | 100.0 |
| 2 | 0.536 | 0.478 | 0.504 | 0.506 | 104.2 |
| 5 | 0.371 | 0.445 | 0.400 | 0.405 | 83.5 |
| 7 | 0.384 | 0.384 | 0.424 | 0.397 | 81.8 |
| 9 | 0.389 | 0.354 | 0.362 | 0.368 | 75.8 |
| Sol | | | | | |
| 0 | 0.368 | 0.376 | 0.331 | 0.358 | 100.0 |
| 2 | 0.284 | 0.257 | 0.266 | 0.269 | 75.1 |
| 5 | 0.053 | 0.217 | 0.192 | 0.154 | 43.0 |
| 7 | 0.042 | 0.026 | 0.156 | 0.075 | 20.8 |
| 9 | 0.033 | 0.019 | 0.023 | 0.025 | 7.0 |
| UDCA | | | | | |
| 0 | 0.416 | 0.402 | 0.406 | 0.408 | 100.0 |
| 2 | 0.402 | 0.397 | 0.400 | 0.399 | 97.9 |
| 5 | 0.425 | 0.413 | 0.423 | 0.420 | 103.0 |

TABLE 3F-continued

Stability of UDCA solution according to Example IV at pH 10, 50° C.

| Day | #1 | #2 | #3 | Average | Percentage |
|---|---|---|---|---|---|
| 7 | 0.406 | 0.402 | 0.408 | 0.406 | 99.4 |
| 9 | 0.424 | 0.426 | 0.421 | 0.423 | 103.8 |

Example V

Solution dosage forms that were prepared according to the following guidelines did not show any precipitation at any pH within the selected, desired pH range. This formulation is based on the known analytical data for pharmaceutical use of bear bile.

| | |
|---|---|
| Tauro UDCA | 7 g |
| Tauro CDCA | 1 g |
| Glyco UDCA | 0.8 g |
| Glyco CDCA | 0.2 g |
| Soluble UDCA | 1 g (or 3 g as free form) |
| Aqueous soluble starch conversion product | 250 g. |
| Sweetener | q.s. |
| Flavoring agent | q.s. |
| Purified water to | 2.0 L |

Soluble UDCA is dissolved in water and then high molecular weight aqueous soluble starch conversion product and water are added. Into the resulting clear solution, Tauro UDCA, Tauro CDCA, Glyco UDCA, Glyco CDCA, sweetener, and flavoring agent were added. Purified water was added to adjust the total volume to be 2.0 L.

Example VI

Figure 2:
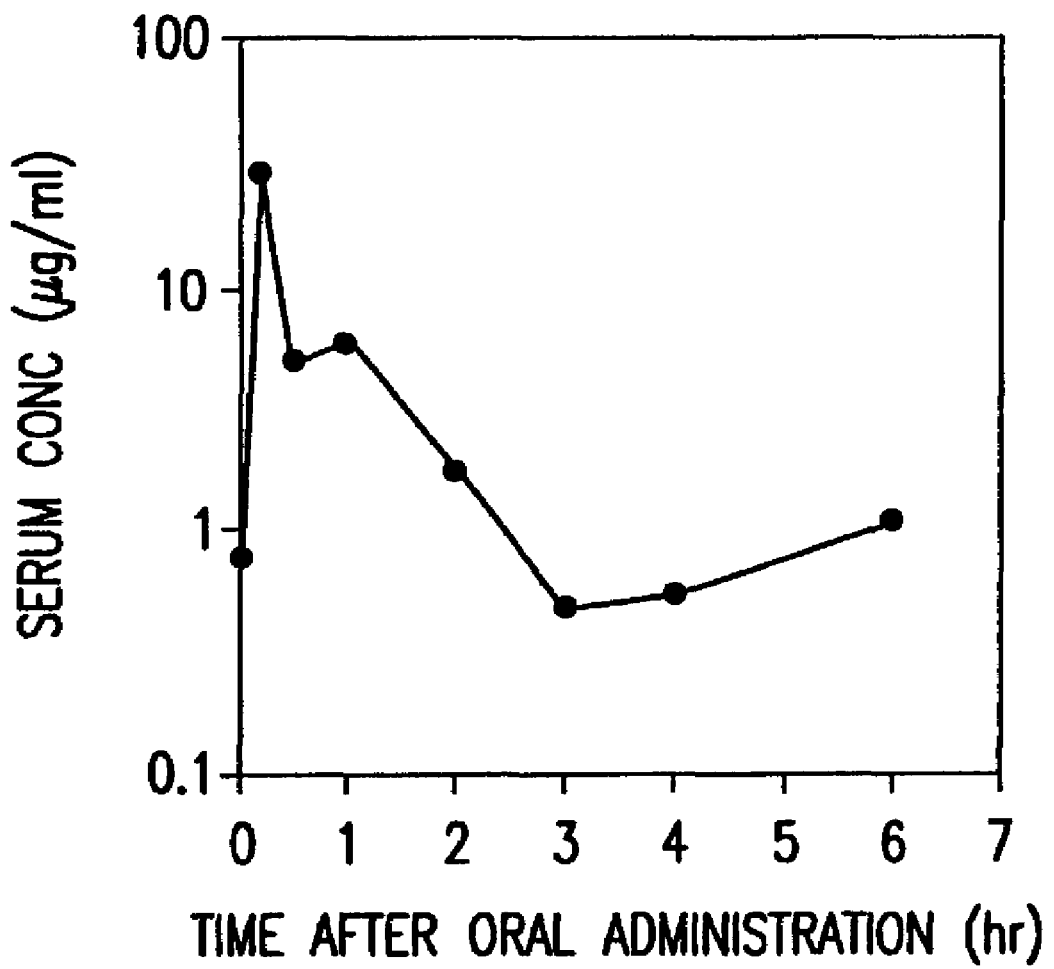
FIG. 2: Graph of blood serum concentration of UDCA versus time following administration of dosage formulations of the bile acid according to Examples III and VI and Table 4.

The aqueous solution dosage forms, according to this invention, containing 200 mg of ursodeoxycholic acid (UDCA), were prepared according to the method described in the above-described Example III and were administered to three healthy men having normal body weight after fasting. The hematic levels of UDCA and glyco UDCA were evaluated by means of well known chemical methods. After applying buffered serum to sep-pak column, methanol eluate was derivatized with phenacyl bromide at 80° C. for 45 minutes. These phenacyl bromide derivatives were dissolved in acetonitrile in preparation for HPLC. The experimental results of the absorption measured at certain times after dosage administration include the total absorption expressed as the area under the serum concentration-time curve (AUC: μg/mL×hours), the maximum hematic concentration ($C_{max}$; μg/mL) that has been obtained, and the time ($T_{max}$; hour) in which said maximum concentration has been obtained. These results are reported in Table 4, FIG. 1, and FIG. 2.

The experimental pharmacokinetic tests of the aqueous solution dosage forms according to this invention carried out on men show substantial improvement in AUC, $C_{max}$ and $T_{max}$ in comparison with the best results from any dosage forms known presently. The maximum hematic concentration ($C_{max}$) in Table 4 shows an average of 8.43±1.69 μg/mL which is at least two times higher than that reported for use of enteric coated sodium salt of UDCA preparations and four times higher than that obtained using regular UDCA tablet preparations. Moreover, the time of peak concentration ($T_{max}$) which is related closely to the rate of absorption of UDCA from the aqueous solution dosage forms is 0.25 hours, at least three times faster than the fastest $T_{max}$ previously known.

Table 4A and Table 4B show plasma concentration of UDCA and GUDCA measured in 3 men over time following on oral administration of the UDCA and GUDCA containing formulations according to Example VI and comparison of results against results of others employing different pharmaceutical formulations of UDCA.

Table 5 shows phamacokinetic parameters of UDCA in human after an oral administration of liquid formulation of UDCA. $C_{max}$ is shown.

Figure 3:
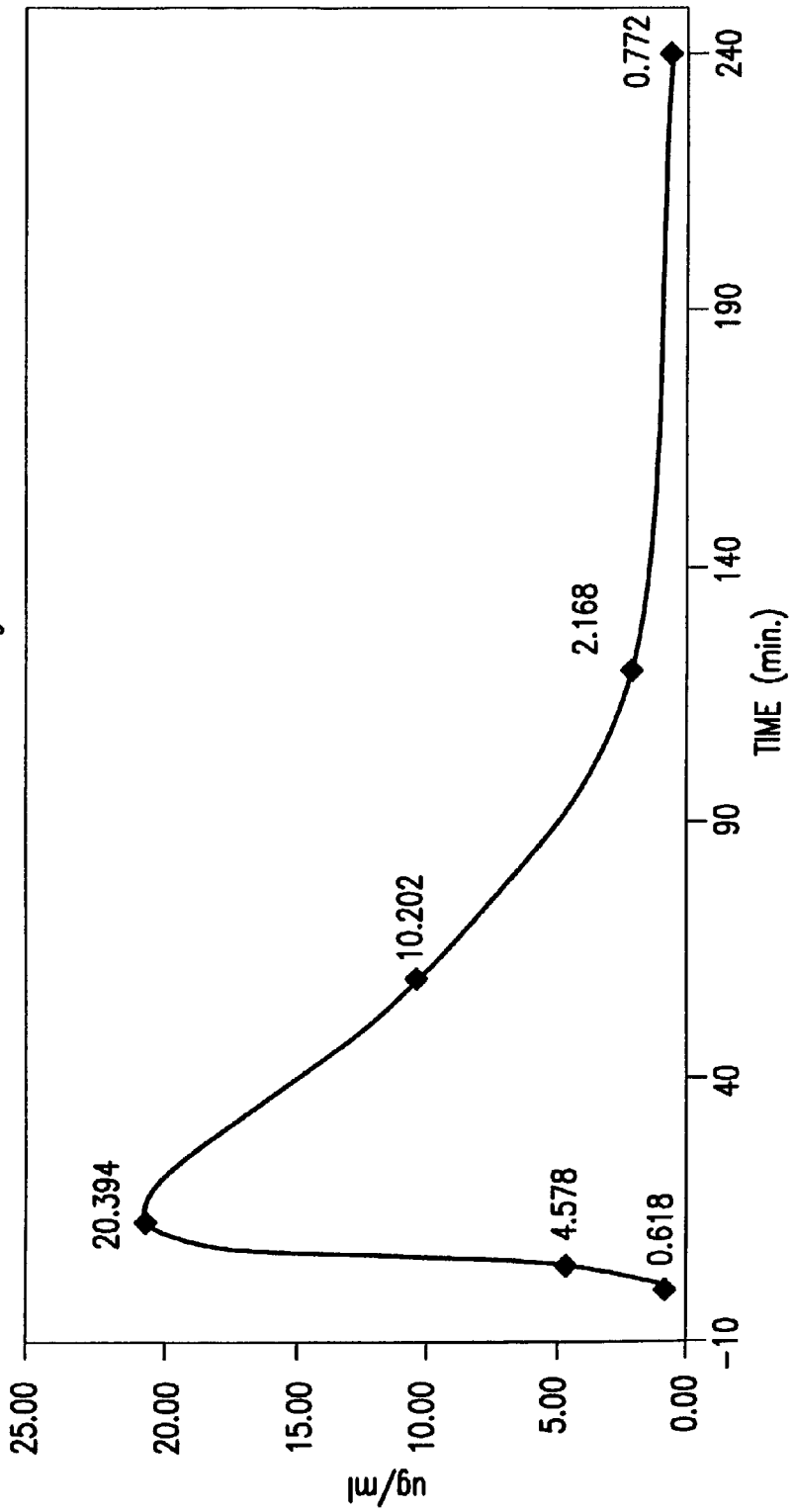
FIG. 3: Diagram of the mean(n=5) for group I for pharmacokinetic parameters of UDCA in human after an oral administration of liquid formulation of UDCA prepared according to Example IX without bismuth.
Figure 4:
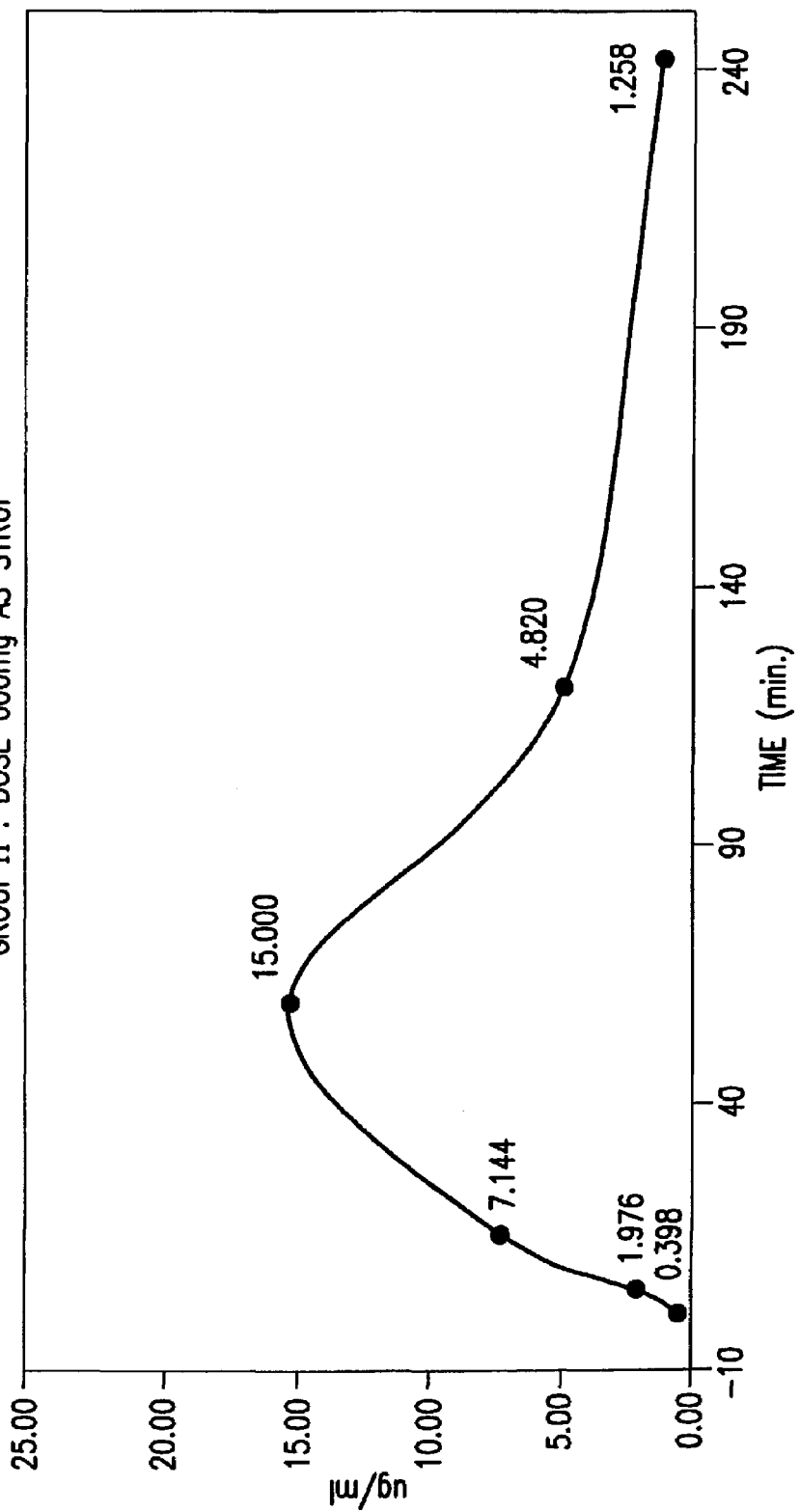
FIG. 4: Diagram of the mean(n=5) for group II for pharmacokinetic parameters of UDCA in human after an oral administration of liquid formulation of UDCA prepared according to Example IX.

Taken together, the data in Tables 4 and 5 and FIGS. 3 and 4 illustrate the supperiority of formulations of the instant invention over conventional formulations with respect to $C_{max}$ and $T_{max}$. the instant The inventive solutions were effect without any break-down of the solution system caused by the pH of the environment in the stomach and intestines. The therapeutic potential of bile acid and possibly even added pharmaceuticals may be more fully realized using the forulations of the invention. When the therapeutically active ingredients in aqueous solution forms are not precipitated as solid by acidic gastric juices in the stomach and by the various alkaline pH levels of the intestine, the formulation overcomes as a natural consequence, the scarce bioavailability resulted by the unexpected, undesirable results for the extent and the rate of release by disintegration, dissolution and/or diffusion should be overcome.

TABLE 5A

Pharmacokinetic parameter ($C_{max}$) of UDCA in human after oral administration of a liquid solution containing 600 mg UDCA per day.

| Time (min) | Person #1 | Person #2 | Person #3 | Person #4 | Person #5 | Average | Std Dev |
|---|---|---|---|---|---|---|---|
| 0 | 0.35 | 1.63 | 0.40 | 0.00 | 0.71 | 0.618 | 0.619 |
| 5 | 2.51 | 9.79 | 1.68 | 2.65 | 6.26 | 4.578 | 3.405 |
| 15 | 12.50 | 47.46 | 8.34 | 11.84 | 21.83 | 20.394 | 15.933 |
| 60 | 9.72 | 6.46 | 7.77 | 9.81 | 17.25 | 10.202 | 4.183 |
| 120 | 3.77 | 1.71 | 1.40 | 1.15 | 2.81 | 2.168 | 1.097 |
| 240 | 0.65 | 0.93 | 0.50 | 0.48 | 1.30 | 0.772 | 0.346 |

TABLE 5B

Pharmacokinetic parameter ($C_{max}$) of UDCA in human after an oral administration of a syrup containing 600 mg UDCA per day.

| Time (min) | Person #1 | Person #2 | Person #3 | Person #4 | Person #5 | Average | Std Dev |
|---|---|---|---|---|---|---|---|
| 0 | 0.62 | 0.58 | 0.38 | 0.00 | 0.41 | 0.398 | 0.246 |
| 5 | 2.76 | 2.63 | 0.83 | 1.42 | 2.24 | 1.976 | 0.827 |
| 15 | 7.80 | 4.45 | 3.54 | 5.85 | 14.08 | 7.144 | 4.197 |
| 60 | 16.08 | 20.33 | 8.76 | 12.06 | 17.77 | 15.000 | 4.605 |
| 120 | 3.98 | 4.24 | 5.09 | 7.79 | 3.00 | 4.820 | 1.820 |
| 240 | 0.81 | 0.99 | 1.47 | 1.85 | 1.17 | 1.258 | 0.411 |

TABLE 4A

Plasma concentration of UDCA and GUDCA after an oral administration of this invention at a dose of 200 mg to three men

| | UDCA | | | | GUDCA | | | |
|---|---|---|---|---|---|---|---|---|
| Time(h) | #1 | #2 | #3 | mean | #1 | #2 | #3 | mean |
| 0.25 | 5.1202 | 10.9171 | 9.159 | 8.43 ± 1.69 | 0.1419 | 0.4549 | 0.3328 | 0.31 ± 0.09 |
| 0.5 | 4.4528 | 7.7432 | 7.4395 | 6.55 ± 1.05 | 0.2564 | 1.2455 | 0.864 | 0.79 ± 0.29 |
| 1 | 1.6921 | 1.546 | 0.2163 | 1.15 ± 0.47 | 0.2162 | 0.6926 | 0.2142 | 0.37 ± 0.16 |
| 1.5 | 0.5256 | 0.2759 | 0.168 | 0.32 ± 0.11 | 1.1573 | 0.1929 | 0.4752 | 0.61 ± 0.29 |
| 2 | 0.2349 | 0.2176 | 0.1227 | 0.19 ± 0.03 | 0.4013 | 0.0312 | 0.0657 | 0.17 ± 0.12 |
| 3 | 0.1237 | N.D. | 0.2074 | 0.17 ± 0.04 | 0.5085 | 0.4303 | 0.3315 | 0.42 ± 0.05 |
| 5 | | | | | 1.9205 | 0.0229 | 1.6311 | 1.18 ± 0.61 |
| 7 | | | | | 0.5328 | 0.4797 | 0.91 | 0.64 ± 0.14 |
| AUC (μg · h/mL) | 4.32 | 6.6 | 5.47 | 5.46 ± 0.66 | 6.26 | 2.22 | 4.65 | 4.38 ± 1.17 |
| $C_{max}$ (μg/mL) | 5.21 | 10.92 | 9.16 | 8.43 ± 1.69 | 1.92 | 1.25 | 1.63 | 1.6 |
| $T_{max}$(h) | 0.25 | 0.25 | 0.25 | 0.25 | 5 | 0.5 | 5 | 3.5 ± 1.5 |

TABLE 4B

Pharmacokinetic parameters of UDCA in human after an oral administration of UDCA (M ± S.E.)

| | $C_{max}$ (ug/mL) | $T_{max}$ (hr) |
|---|---|---|
| Roda et al. (1994) | | |
| UDCA gelatine capsule, 450 mg | 2.59 | 3.8 |
| NaUDC gelatine capsule, 475 mg | 3.42 | 2.4 |
| NaUDC enteric-coated, 475 mg | 10 | 3.4 |
| Nagamatsu et al. (1997) | | |
| UDCA 200 mg | 1.9 ±0.25 | 1.5 ± 0.4 |
| UDCA 400 mg | 7.09±1.43 | 0.8 ± 0.2 |
| UDCA in this invention, 200 mg | 8.43±1.69 | 0.25 |

Example VII

Solution dosage forms that were prepared according to the following guidelines did not show any precipitation at any pH within the selected desired range of pH values.

| | |
|---|---|
| Soluble UDCA | 0.2 g (0.05 g–2 g as free acid) |
| Dried powder of liquid glucose (Commercial corn syrup solid) | 20 g (3 g–120 g) |
| Soluble non starch polysaccharide (Guar gum or pectin, etc.) | 0.01 g (0.001 g–0.05 g) |
| Purified water to make | 100 mL |

85 mL of the aqueous solution in which soluble UDCA is dissolved was prepared, and then the mixture of dried powder of liquid glucose, a high molecular weight aqueous soluble starch conversion product and a soluble non starch polysaccharide (guar gum, pectin, etc.) was added into the clear solution. Purified water was added to adjust the total volume to 100 mL.

Example VIII

Mixture Solution

The formulations of Examples VIII, IX, X, XI, and XII include aqueous soluble bismuth chelate. In each of these examples, solution dosage forms were prepared by adding an amount of an ammonium salt of bismuth sulfate sufficient to provide the indicated amount of bismuth sulfate.

Solution dosage forms that were prepared according to the following guidelines did not show any precipitation at any pH within the selected desired range of pH values.

| | |
|---|---|
| UDCA | 5 g |
| CDCA | 5 g |
| Bismuth citrate | 5 g |
| Corn syrup solid | 260 g |
| Citric acid | q.s. |
| Purified water to make | 1.0 L |

The UDCA and CDCA were first dissolved in 1.5 mL of a 1N NaOH solution. Next, to the resulting clear solution were added the bismuth sulfate and 150 mL of water. Then, the corn syrup solid was added portion by portion with vigorous agitation. The resulting solution was titrated to pH 4 with citric acid. Purified water was added to adjust the total volume to 1.0 L.

Example IX

UDCA-Syrup (20 g UDCA/L)

Solution dosage forms that were prepared according to the following guidelines did not show any precipitation at any pH within the selected desired range of pH values.

| | |
|---|---|
| UDCA | 20 g |
| 1 N NaOH | 60 mL |
| Maltodextrin | 700 g |
| Bismuth citrate | 4 g |
| Citric acid or lactic acid | q.s. |
| Purified water to make | 1.0 L |

The UDCA is first dissolved in 60 mL of a 1N NaOH solution. Next, to the resulting clear solution were added the bismuth sulfate and 150 mL of water. Then, the maltodextrin was added portion by portion with vigorous agitation. The resulting solution was titrated to pH 3.5 with citric acid. Purified water was added to adjust the total volume to 1.0 L.

Example X

UDCA-Syrup (20 g UDCA/L)

Solution dosage forms that were prepared according to the following guidelines did not show any precipitation at any pH within the selected desired range of pH values.

| | |
|---|---|
| UDCA | 20 g |
| 1 N NaOH | 60 mL |
| Corn syrup solid | 1,050 g |
| Bismuth citrate | 4 g |
| Citric acid or lactic acid | q.s. |
| Purified water to make | 1 L |

The UDCA is first dissolved in 60 mL of a 1N NaOH solution. Next, to the resulting clear solution were added the bismuth sulfate and 280 mL of water. Then, 1,050 g of corn syrup solid was added portion by portion with vigorous agitation. The resulting solution was titrated to pH 3.5 with citric acid. Purified water was added to adjust the total volume to 1.0 L.

Example XI

UDCA-Thick Syrup (30 g UDCA/L)

Solution dosage forms that were prepared according to the following guidelines did not show any precipitation at any pH within the selected desired range of pH values.

| | |
|---|---|
| UDCA | 30 g |
| 1 N NaOH | 90 mL |
| Maltodextrin | 1,050 g |
| Citric acid or lactic acid | 50 g |
| Purified water to make | 1.0 L |

The UDCA is first dissolved in 90 mL of a 1N NaOH solution. Next, to the resulting clear solution were added the bismuth sulfate and 250 mL of water. Then, 1,050 g of maltodextrin was added portion by portion with vigorous agitation. The resulting solution was titrated to pH 3 by the addition of 50 g of citric acid. Purified water was added to adjust the total volume to 1.0 L.

Example XII

UDCA-Thick Syrup (30 g UDCA/L)

Solution dosage forms that were prepared according to the following guidelines did not show any precipitation at any pH within the selected desired range of pH values.

| | |
|---|---|
| UDCA | 30 g |
| 1 N NaOH | 90 mL |
| Corn syrup solid | 1,500 g |
| Citric acid or lactic acid | 50 g |
| Purified water to make | 1.0 L |

The UDCA is first dissolved in 90 mL of a 1N NaOH solution. Next, to the resulting clear solution were added the bismuth sulfate and 230 mL of water. Then, 1,500 g of corn syrup solid was added portion by portion with vigorous agitation. The resulting solution was titrated to pH 3 by the addition of 50 g of citric acid. Purified water was added to adjust the total volume to 1.0 L.

Example XIII

UDCA-Paste (45 g UDCA/L)

The formulations of Examples XIII, XIV, XV, XVI, XVII, and XVIII include bismuth citrate as chelate. In each of these examples, solution dosage forms were prepared by adding an amount of an ammonium salt of bismuth citrate sufficient to provide the indicated amount of bismuth citrate.

Solution dosage forms that were prepared according to the following guidelines did not show any precipitation at any pH within the selected desired range of pH values.

| | |
|---|---|
| UDCA | 45 g |
| 1 N NaOH | 135 mL |
| Maltodextrin | 1,575 g |
| Bismuth citrate | 10 g |
| Citric acid or lactic acid | q.s. |
| Purified water to make | 1.0 L |

The UDCA is first dissolved in 135 mL of a 1N NaOH solution. Next, to the resulting clear solution were added the bismuth citrate and 200 mL of water. Then, 1,575 g of maltodextrin was added portion by portion with vigorous agitation. The resulting solution was titrated to pH 3 by the addition of citric acid. Purified water was added to adjust the total volume to 1.0 L.

Five human subjects were provided with dosage forms prepared according to this Example. The results are shown in Tables 5A and 5B and rendered graphically in FIGS. 3 and 4. A comparison of the sharp peak of FIG. 3 with the broad peak of FIG. 4 indicates that, by adjusting the dosage form, a practitioner may manipulate the bile acid $C_{max}$ and $T_{max}$.

Figure 5A:
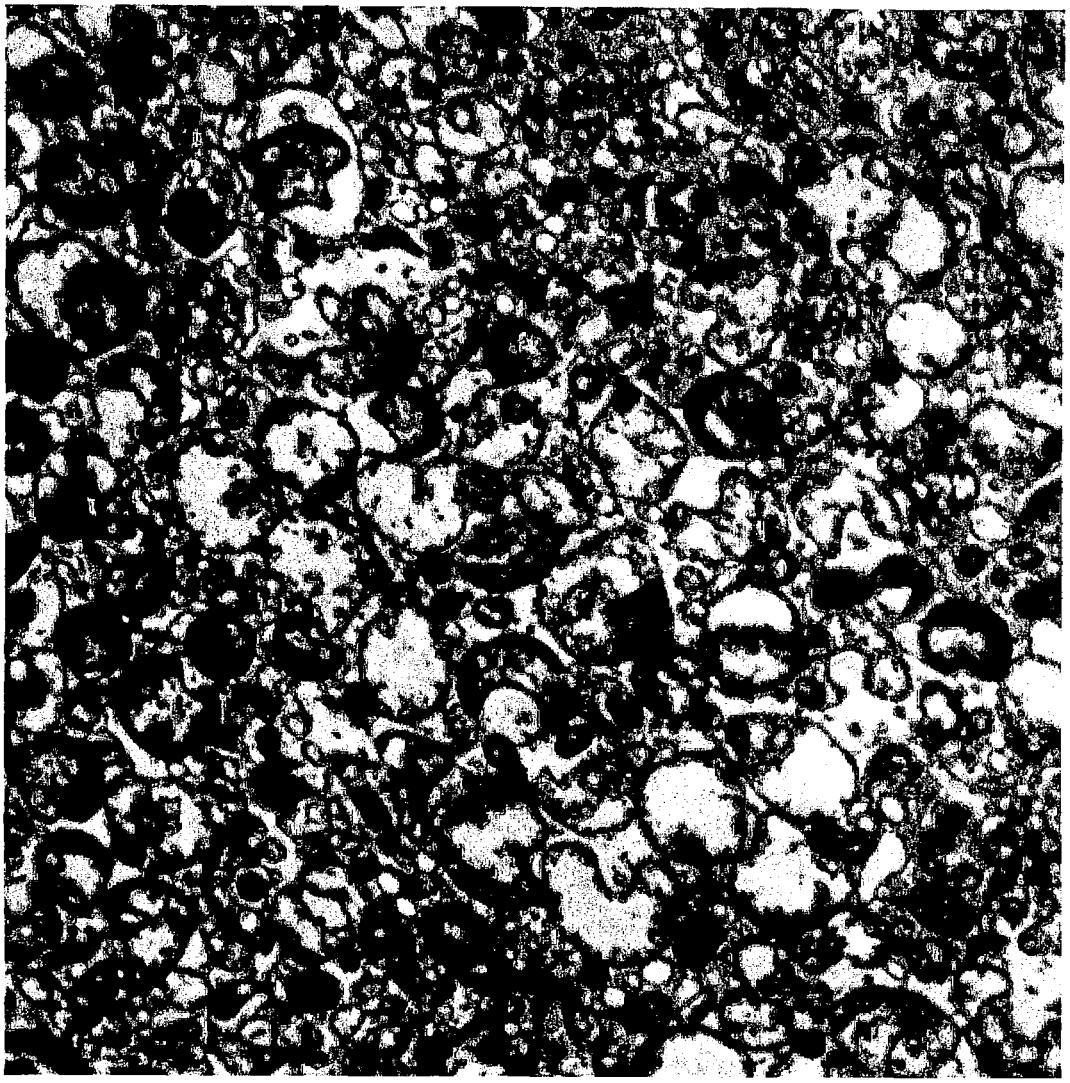
FIG. 5A. Transmission electron micrograph of *H. pylori* cultured from Columbia medium.
Figure 5B:
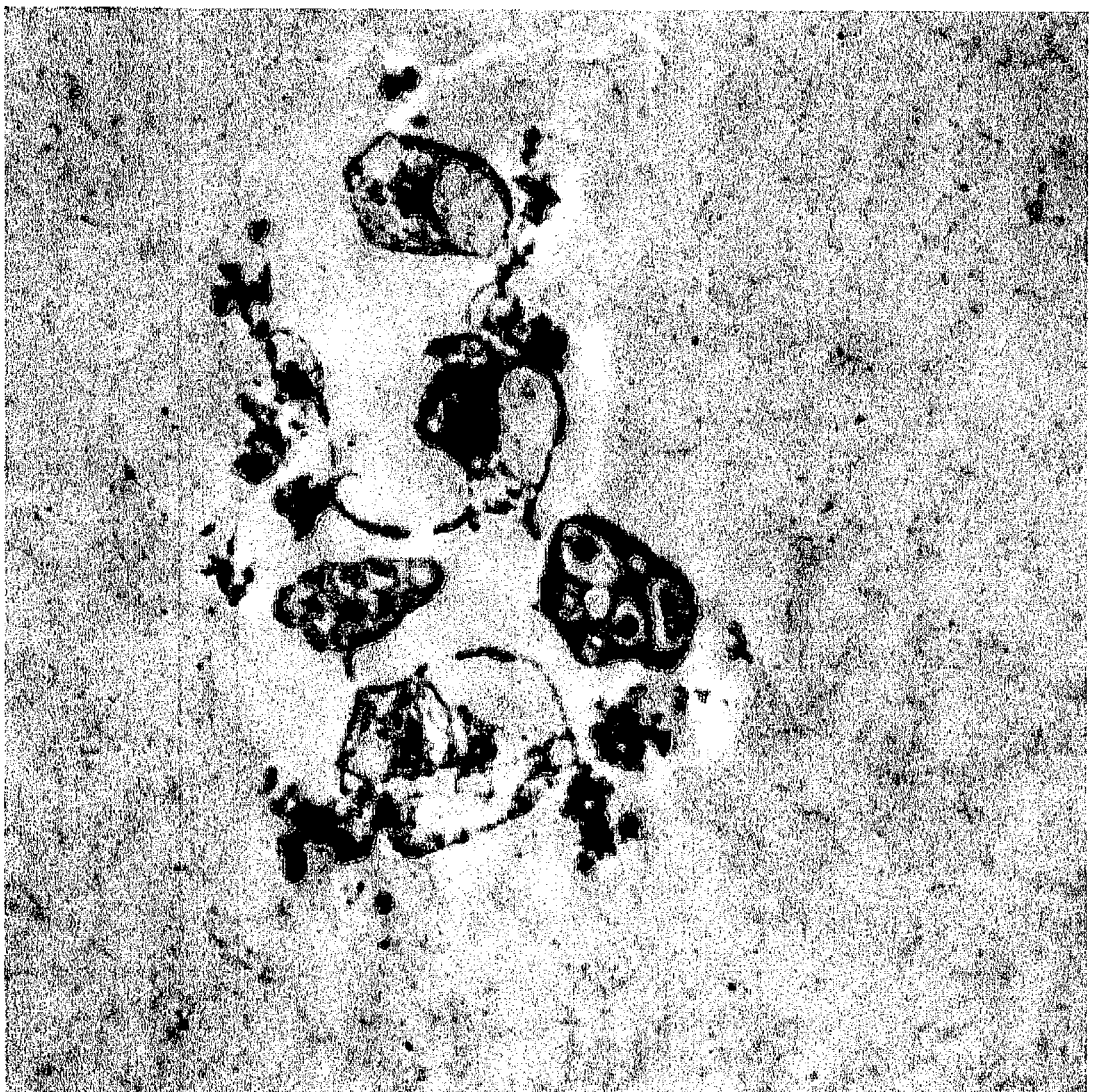
FIG. 5B. Transmission electron micrograph of *H. pylori* 48 hrs after being treated with UDCA & bismuth citrate prepared according to Example IX.
Figure 5C:
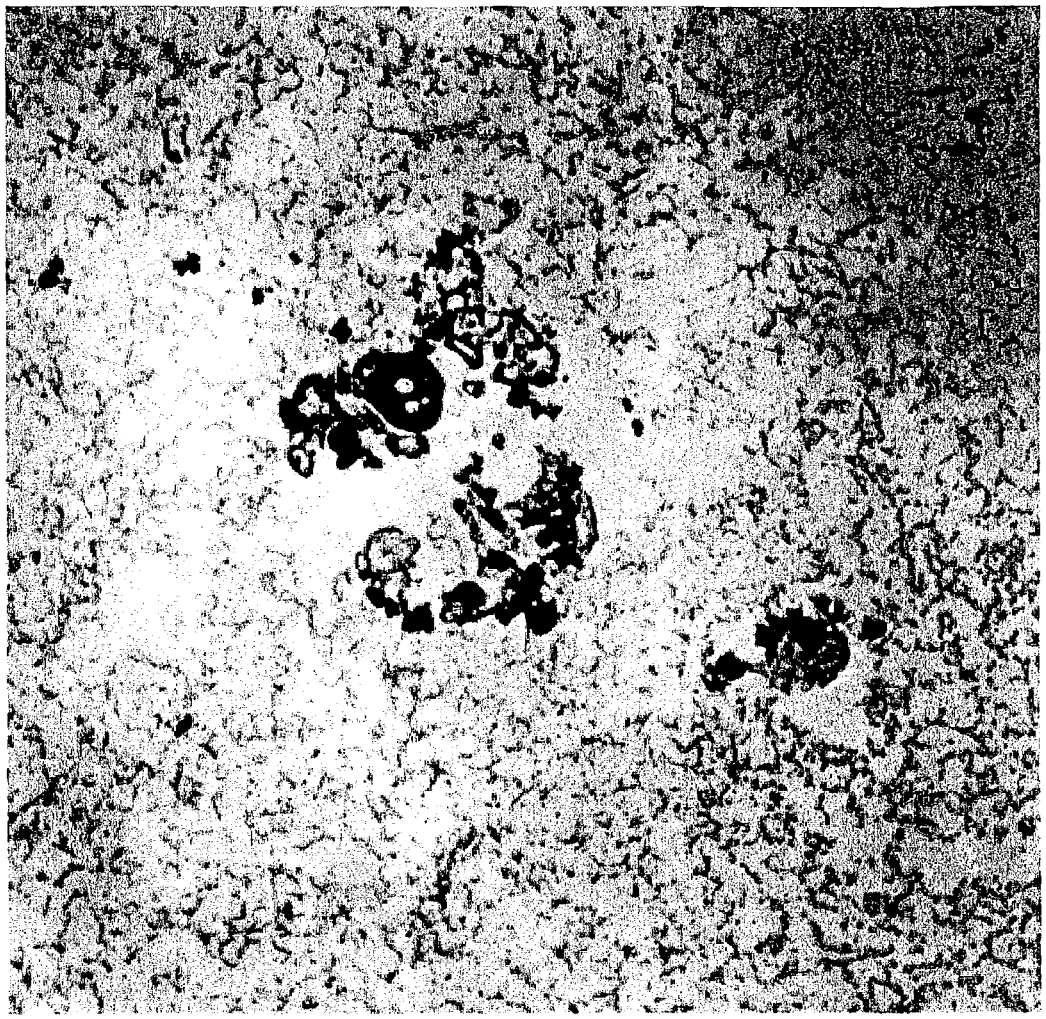
FIG. 5C. Transmission electron micrograph of *H. pylori* 72 hrs after being treated with UDCA & bismuth citrate.

H. pylori were cultured on Columbia Bood Agar Base (CRAB) media containing a preparation of Example IX. 2 L of CRAB plates were prepared which contained 9.9 g of CRAB, 9.1 g of tryptic soy agar, 50 mL of sheeps blood, vacomycin, amphotericin B, polymixin B, 2 mL of Example IX, and 358 mL distilled water. After 48 or 72 hours of microaerophillic incubation, bateria were fixed using Karnovsky's fixative and embedded in epon. Electron micrographs of H. pylori cells are shown in figures FIGS. 5A to 5C.

Example XIV

UDCA-Paste (45 g UDCA/L)

Solution dosage forms that were prepared according to the following guidelines did not show any precipitation at any pH within the selected desired range of pH values.

| | |
|---|---|
| UDCA | 45 g |
| 1 N NaOH | 135 mL |
| Corn syrup solid | 2,300 g |
| Citric acid or lactic acid | 50 g |
| Purified water to make | 1.0 L |

The UDCA is first dissolved in 135 mL of a 1N NaOH solution. Next, to the resulting clear solution were added the bismuth citrate and 150 mL of water. Then, 2,300 g of corn syrup solid was added portion by portion with vigorous agitation. The resulting solution was titrated to pH 3 by the addition of citric acid. Purified water was added to adjust the total volume to 1.0 L.

Example XV

Mixture solution of UDCA (22 g) and CDCA (3 g)

Solution dosage forms that were prepared according to the following guidelines did not show any precipitation at any pH within the selected desired range of pH values.

| | |
|---|---|
| UDCA | 22 g |
| 1 N NaOH | 75 mL |
| CDCA | 3 g |
| Maltodextrin | 875 g |
| Bismuth citrate | 4 g |
| Citric acid or lactic acid | q.s. |
| Purified water to make | 1.0 L |

The UDCA and CDCA are first dissolved in 75 mL of a 1N NaOH solution. Next, to the resulting clear solution were added the bismuth citrate and 240 mL of water. Then, 875 g of maltodextrin was added portion by portion with vigorous agitation. The resulting solution was titrated to pH 3 by the addition of citric acid. Purified water was added to adjust the total volume to 1.0 L.

Example XVI

Mixture solution of UDCA (22 g) and CDCA (3 g)

Solution dosage forms that were prepared according to the following guidelines did not show any precipitation at any pH within the selected desired range of pH values.

| | |
|---|---|
| UDCA | 22 g |
| 1 N NaOH | 75 mL |
| CDCA | 3 g |
| Corn syrup solid | 1,320 g |
| Bismuth citrate | 4 g |
| Citric acid or lactic acid | q.s. |
| Purified water to make | 1.0 L |

The UDCA and CDCA are first dissolved in 75 mL of a 1N NaOH solution. Next, to the resulting clear solution were added the bismuth citrate and 240 mL of water. Then, 1,320 g of corn syrup solid was added portion by portion with vigorous agitation. The resulting solution was titrated to pH 3 by the addition of citric acid. Purified water was added to adjust the total volume to 1.0 L.

Example XVII

The effect of treating H. pylori infected mice with a solution dosage form of the invention was tested. Six week old C57BL/6 female mice were infected by feeding at diet comprising $10^9$ CFU/mL H. pylori, SS1 strain. The animals consumed this feed twice, one week apart. Subsequently, 0.2 mL of a solution dosage form according to Example VIII was administered to four infected animals once per day for one week. Two animals were sacrificed one week following administration of the last dose of the inventive solution. The remaining two animals were sacrificed four weeks following administration of the last dose of the inventive solution.

Whole stomachs were washed with saline to remove mucosa and debris. A sample of stomach tissue from each animal was subjected to a CLO test using a rapid urease test kit (Delta West, Australia). Each residual stomach was fixed with 10% formalin solution and embedded with paraffin. Sections (4 μm thick) were collected on glass slides and stained with H&E staining solution and Warthin staining solution. Tissue was evaluated for pathological status by conventional light microscopy.

The results, summarized in Table 6, indicate that the urease test results were negative for mice passed one week after discontinuing administration of the liquid dosage form, and *H. pylori* was not seen in Warthin examination. Of the other two mice, one showed a negative urease test and no *H. pylori* were seen by Warthin examination. The other, however, yielded a positive urease test although only a few *H. pylori* were seen in Warthin examination.

TABLE 6

| Weeks After Treatment | Animal | Urease Test | Warthin Examination |
|---|---|---|---|
| 1 | 1 | Negative | No *H. pylori* |
| 1 | 2 | Negative | No *H. pylori* |
| 4 | 3 | Negative | No *H. pylori* |
| 4 | 4 | Positive | A few *H. pylori* |

Example XVIII

Assays for growth of *H. pylori* on media containing UDCA, bismuth citrate or both UDCA and bismuth citrate were performed. For these assays the following media was used:

000112B-1 having a pH of 4.0 and comprising 525 g/L maltodextrin and 15 g/L UDCA.

OSABY having a pH of 3.7 and comprising 1 kg/L corn syrup solid and 6 g/L bismuth citrate.

Three assays were performed to assess the growth capacity of *H. pylori* in the presence of UDCA, bismuth or both wherein the pH, concentration, and length of exposure was varied.

Figure 9:
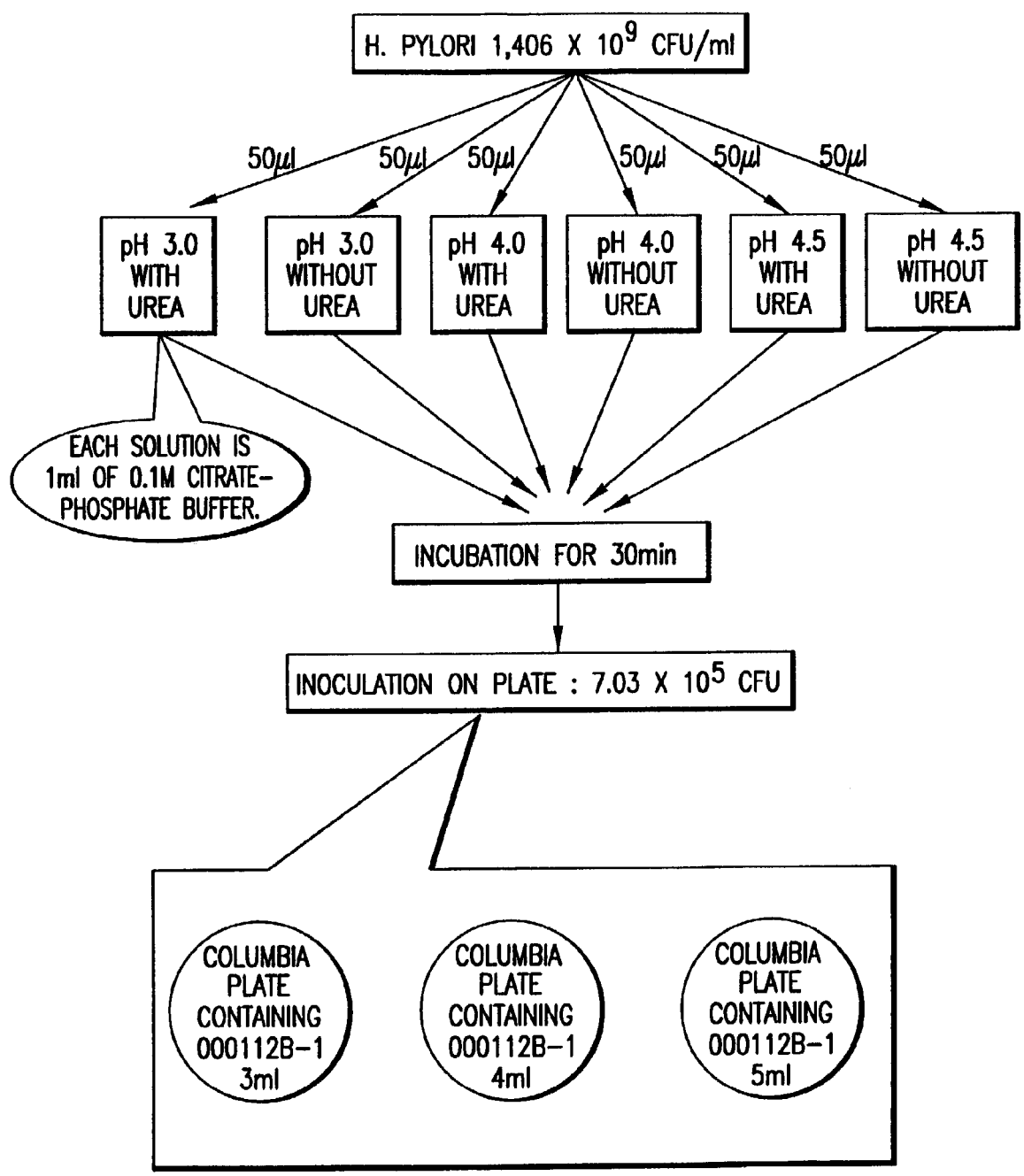
FIG. 9: *H. pylori* culture method.

1. *Helicobacter pylori* was suspended in physiological saline to give about $10^9$ organisms per milliliter. 50 μL of this innoculum was transferred to tubes containing 1 mL of citrate-phosphate buffer at pH 3.0, 4.0, and 4.5. Paired tubes were prepared with and without 6 mM Urea. Following a 30 minute room temperature incubation, the suspensions were subcultured on agar plates containing 000112B-1 using a 1 μL loop. Plates were incubated microaerophilically at 37° C. for 72 hours. This procedure is illustrated in FIG. 9.

As shown in Table 7, *H. pylori* grew poorly on pH 3 and pH 4 control media. Table 7 further shows that *H. pylori* does not grow on pH 3 and pH 4 media containing UDCA. The designations "3 ml", "4 ml" and "5 ml" refer to the total volume of 000112B-1 media per plate. "PBS" is phosphate buffered saline at pH 7.0.

TABLE 7

| Plate | pH | Urea | Urease Test | | | |
|---|---|---|---|---|---|---|
| | | | 1–2 sec. | 10 min. | 2 hr. | 20 hr. |
| Control | 3.0 | Yes | FO | FO | O | O |
| | | No | FO | FO | O | O |
| | 40 | Yes | FO | FO | O | O |
| | | No | FO | FO | O | P |
| | 4.5 | Yes | FP | FP | P | P |
| | | No | FO | O | FP | P |
| | PBS | Yes | O | FP | P | P |
| | | No | O | FP | P | P |
| 000112B-1 (3 mL) | 3.0 | Yes | Y | Y | Y | Y |
| | | No | Y | Y | Y | Y |
| | 4.0 | Yes | Y | Y | FO | O |
| | | No | Y | Y | Y | FO |
| | 4.5 | Yes | FP | FP | P | P |
| | | No | FP | FP | P | P |
| 000112B-1 (4 mL) | 3.0 | Yes | Y | Y | Y | Y |
| | | No | Y | Y | Y | Y |
| | 4.0 | Yes | Y | Y | Y | FO |
| | | No | Y | Y | FO | FO |
| | 4.5 | Yes | FP | FP | P | P |
| | | No | FP | FP | FP | P |
| 000112B-1 (5 mL) | 3.0 | Yes | Y | Y | Y | Y |
| | | No | Y | Y | Y | Y |
| | 4.0 | Yes | Y | Y | FO | FO |
| | | No | Y | Y | Y | Y |
| | 4.5 | Yes | FP | FP | P | P |
| | | No | FP | FP | P | P |

Key

| Y | FO | O | FP | P |
|---|---|---|---|---|
| Color Yellow | Faint Orange | Orange | Faint Pink | Pink |
| Helicobacter None | Very Rare | Rare | Exist | Many |

Figure 10:
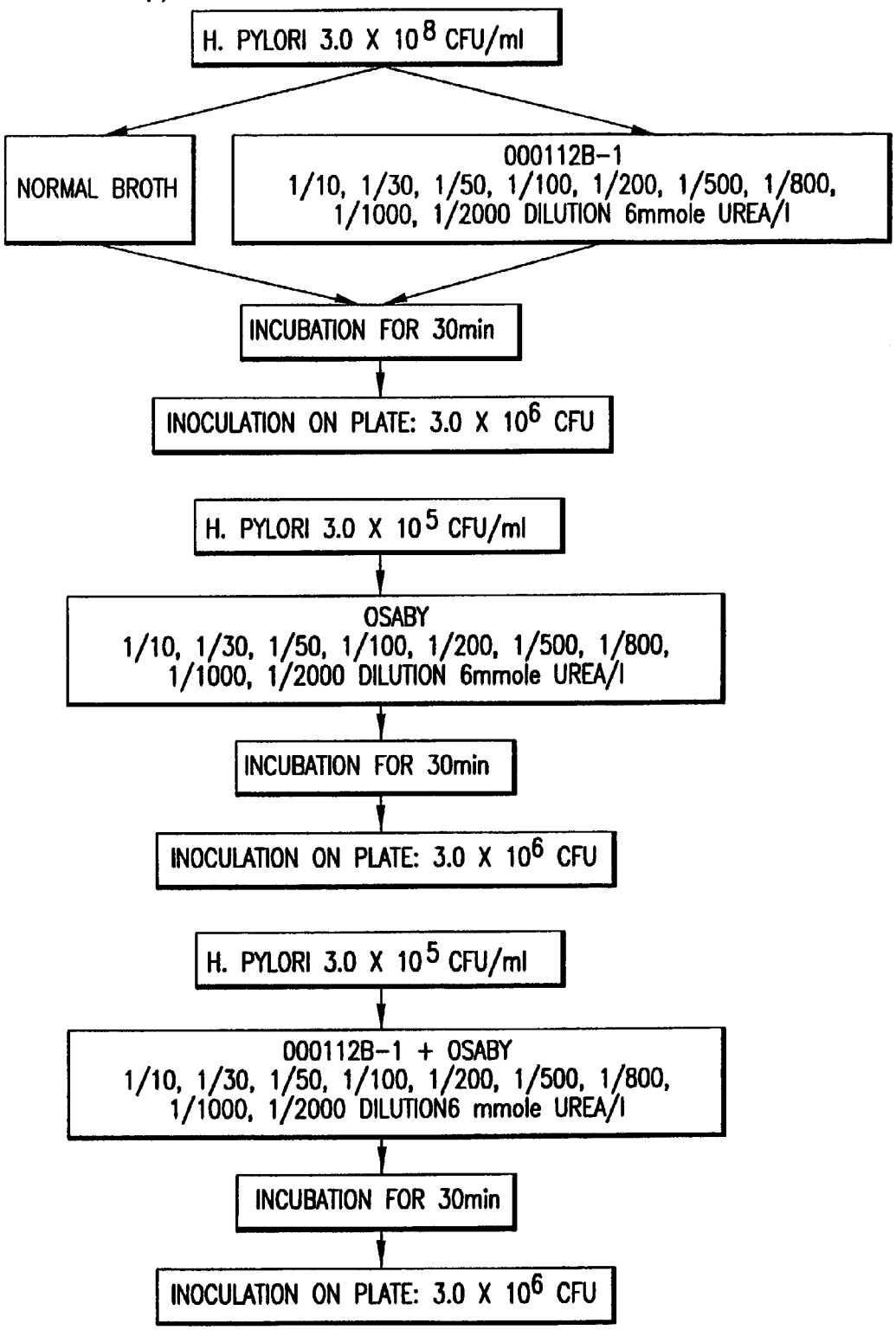
FIG. 10: *H. pylori* culture method.

2. *Helicobacter pylori* was suspended in physiological saline to give about $10^9$ organisms per milliliter. 50 μL of this innoculum was transferred to tubes containing 1 mL of citrate-phosphate buffer at various concentrations of plating media such as 1/10, 1/30, 1/50, 1/100, 1/200, 1/500, 1/800, 1/1000, 1/2000. All tubes were prepared with 6 mM Urea. Following a 30 minute room temperature incubation, the suspensions were subcultured on agar plates using a 1 μL loop. These plates were substantially free of bismuth and bile acids. Plates were incubated microaerophilically at 37° C. for 72 hours. This procedure is illustrated in FIG. 10.

Table 8 shows urease test results following 72 hours of growth of *H. pylori* on media prepared with dilutions of UDCA (000112B-1) bismuth citrate (OSABY) or both UDCA and bismuth citrate. Poor growth of *H. pylori* on media containing either UDCA or bismuth citrate was observed (Table 8). Growth of *H. pylori* was further attenuated when cultured on media containing both UDCA and bismuth citrate (Table 8).

TABLE 8

| Plate | Urease Test | | | |
|---|---|---|---|---|
| | Immediately | 10 min. | 30 min. | 60 min. |
| 000112B-1 | | | | |
| Control | P | P | P | P |
| 1/10 | Y | FP | P | P |
| 1/30 | Y | FP | P | P |
| 1/50 | Y | FP | P | P |
| 1/100 | Y | FP | P | P |
| 1/200 | Y | FP | P | P |
| 1/500 | Y | FP | P | P |
| 1/800 | FP | P | P | P |
| 1/1000 | FP | P | P | P |
| 1/2000 | FP | P | P | P |

TABLE 8-continued

OSABY

| | | | | |
|---|---|---|---|---|
| Control | P | P | P | P |
| 1/10 | Y | FP | P | P |
| 1/30 | Y | FP | P | P |
| 1/50 | Y | FP | P | P |
| 1/100 | FP | FP | P | P |
| 1/200 | FP | FP | P | P |
| 1/500 | FP | FP | P | P |
| 1/800 | FP | P | P | P |
| 1/1000 | FP | P | P | P |
| 1/2000 | FP | P | P | P |
| 000122B-1 + OSABY | | | | |
| Control | P | P | P | P |
| 1/10 | Y | FP | FP | FP |
| 1/50 | Y | Y | Y | Y |
| 1/100 | Y | Y | Y | Y |
| 1/500 | Y | FP | FP | FP |
| 1/1000 | Y | FP | P | P |

Key

| Color | Y | FO | O | FP | P |
|---|---|---|---|---|---|
| Helicobacter | Yellow None | Faint Orange Very Rare | Orange Rare | Faint Pink Exist | Pink Many |

3. *Helicobacter pylori* was suspended in physiological saline to give about $10^9$ organisms per milliliter. 50 µL of this innoculum was transferred to tubes containing 1 mL of citrate-phosphate buffer at various concentrations such as ½, ¼, and ⅒ for 15 minutes, ½, ¼, and ⅒ for 30 minutes, and ½, ¼, and ⅒ for 45 minutes. Paired tubes were innoculated with and without 6 mM Urea. Following a 30 minute room temperature incubation, the suspensions were subcultured on agar plates using a 1 µL loop. These plates were substantially free of bismuth and bile acids. Plates were incubated microaerophilically at 37° C. for 72 hours. This procedure is illustrated in FIG. 11.

Table 9 shows urease test results following 72 hours of growth of *H. pylori* on media prepared with dilutions of UDCA (000112B-1) bismuth citrate (OSABY) or both UDCA and bismuth citrate. As indicated, longer exposure times increased the adverse effect of the solutions on *H. pylori*.

TABLE 9

| | Incubation | Urease Test (min.) | | | | |
|---|---|---|---|---|---|---|
| Dilution | Time (min.) | 1 | 30 | 60 | 120 | 240 |
| 000112B-1 | | | | | | |
| Control | | P | P | P | P | P |
| ½ | 15 | Y | Y | Y | Y | Y |
| | 30 | Y | Y | Y | Y | Y |
| | 45 | Y | Y | Y | Y | Y |
| ¼ | 15 | Y | FO | FP | P | P |
| | 30 | Y | Y | FO | FO | FO |
| | 45 | Y | Y | Y | Y | Y |
| ⅒ | 15 | Y | FO | FO | FO | FO |
| | 30 | Y | FO | FO | O | P |
| | 45 | Y | Y | Y | FO | FO |
| OSABY | | | | | | |
| Control | | P | P | P | P | P |
| ½ | 15 | Y | Y | Y | Y | Y |
| | 30 | Y | Y | Y | Y | Y |
| | 45 | Y | Y | Y | Y | Y |
| ¼ | 15 | Y | Y | Y | Y | Y |
| | 30 | Y | Y | Y | Y | Y |
| | 45 | Y | Y | Y | Y | Y |
| ⅒ | 15 | Y | FO | FO | FO | P |
| | 30 | Y | Y | Y | Y | Y |
| | 45 | Y | Y | Y | Y | Y |
| 000122B-1 + OSABY | | | | | | |
| Control | | P | P | P | P | P |
| ½ | 15 | Y | Y | Y | Y | Y |
| | 30 | Y | Y | Y | Y | Y |
| | 45 | Y | Y | Y | Y | Y |
| ¼ | 15 | Y | Y | Y | Y | Y |
| | 30 | Y | Y | Y | Y | Y |
| | 45 | Y | Y | Y | Y | Y |
| ⅒ | 15 | Y | Y | Y | FO | FO |
| | 30 | Y | FO | FO | FO | P |
| | 45 | Y | Y | Y | Y | Y |

I claim:

1. A method for achieving a $C_{max}$ (µg UDCA/mL) of from about 4.5 to about 20.4 with a $T_{max}$ of less than about 30 minutes comprising:
   (a) administration of a clear oral liquid dosage form comprising:
      (i) a first material selected from the group consisting of a bile acid, an aqueous soluble derivative of a bile acid, a bile acid salt, a bile acid conjugated with an amine by an amide linkage, and combinations thereof;
      (ii) a second material selected from the group consisting of an aqueous soluble starch conversion product and/or an aqueous soluble non-starch polysaccharide; and
      (iii) sodium hydroxide, and,
      (iv) water,
   wherein the first and second materials both remain in solution for all pH values of the solution within a selected range of pH values and wherein the molar ratio of the sodium hydroxide to the first material is from about 0.6 to about 1.2.

2. The method of claim 1 wherein the dosage form is selected from the group consisting of a syrup, a thick syrup, and a paste.

3. The method of claim 1 wherein the first material is selected from the group consisting of ursodeoxycholic acid, ursodeoxycholic acid derivatives at a hydroxyl or carboxylic acid group on the steroid nucleus, ursodeoxycholic acid salts, and ursodeoxycholic acid conjugates with amines.

4. The method of claim 1 wherein the second material is selected from the group consisting of maltodextrin, dextrin, corn syrup, corn syrup solid, soluble starch, and dextrans.

5. The method of claim 1 wherein the oral liquid dosage form comprises one or more additional bile acids, aqueous soluble derivatives of bile acid, bile acid salts, and amine-conjugated bile acids conjugated by an amide linkage.

6. The method of claim 1 wherein the oral liquid dosage form additionally comprises a least one additional agent.

7. The method of claim 1 wherein the additional agent is selected from the group consisting of guar gum, pectin, acacia, carrageenan, carboxymethyl cellulose sodium, hydroxymethyl cellulose, hydroxypropyl cellulose, methyl cellulose, polyvinyl alcohol, povidone, tragacanth gum, xanthan gum, and sorbitan ester.

8. The method of claim 1 wherein the oral liquid dosage form additionally comprises at least one pharmaceutical in a pharmaceutically effective amount.

9. The method of claim 8 wherein the pharmaceutical compound is selected from the group consisting of octreotide, sildenafil citrate, calcitriol, dihydrotachysterol, apomorphine, yohimbine, trazadone, acyclovir, cidofovir, delavirdine-mesylate, didanosine, famciclovir, foscarnet sodium, fluorouracil, ganciclovir sodium, idoxuridine, interferon-α, β, γ, lamivudine, nevirapine, penciclovir, ribavirin, stavudine, triflundine, valacyclovir-HCl, zalcitabine, zidovudine, indinavir-$H_2SO_4$, ritonavir, nelfinavir-$CH_3SO_3H$, saquinavir-$CH_3SO_3H$, d-penicillamine, chloroquine, hydroxychloroquine, aurothioglucose, gold sodium thiomalate, auranofin levamisole, dacarbazine, isoprinosine, methyl inosine monophosphate, muramyl dipeptide, diazoxide, hydralazine-HCl, and minoxidil.

10. A method for achieving a $C_{max}$ (μg GUDCA/mL) of from about 0.3 to about 1.6 with a $T_{max}$ of less than about 3.5 hours comprising:
    (a) administration of a clear oral liquid dosage form comprising:
        (i) a first material selected from the group consisting of a bile acid, an aqueous soluble derivative of a bile acid, a bile acid salt, a bile acid conjugated with an amine by an amide linkage, and combinations thereof;
        (ii) a second material selected from the group consisting of an aqueous soluble starch conversion product and/or an aqueous soluble non-starch polysaccharide;
        (iii) sodium hydroxide, and,
        (iv) water,
wherein the first and second materials both remain in solution for all pH values of the solution within a selected range of pH values and wherein the molar ratio of the sodium hydroxide to the first material is from about 0.6 to about 1.2.

11. The method of claim 10 wherein the dosage form is selected from the group consisting of a syrup, a thick syrup, and a paste.

12. The method of claim 10 wherein the first material is selected from the group consisting of glycoursodeoxycholic acid, glycoursodeoxycholic acid derivatives at a hydroxyl or carboxylic acid group on the steroid nucleus, glycoursodeoxycholic acid salts, and glycoursodeoxycholic acid conjugates with amines.

13. The method of claim 10 wherein the second material is selected from the group consisting of maltodextrin, dextrin, corn syrup, corn syrup solid, soluble starch, and dextrans.

14. The method of claim 10 wherein the oral liquid dosage form comprises one or more additional bile acids, aqueous soluble derivatives of bile acid, bile acid salts, and amine-conjugated bile acids conjugated by an amide linkage.

15. The method of claim 10 wherein the oral liquid dosage form additionally comprises a least one additional agent.

16. The method of claim 15 wherein the additional agent is selected from the group consisting of guar gum, pectin, acacia, carrageenan, carboxymethyl cellulose sodium, hydroxymethyl cellulose, hydroxypropyl cellulose, methyl cellulose, polyvinyl alcohol, povidone, tragacanth gum, xanthan gum, and sorbitan ester.

17. The method of claim 10 wherein the oral liquid dosage form additionally comprises at least one pharmaceutical in a pharmaceutically effective amount.

18. The method of claim 17 wherein the pharmaceutical compound is selected from the group consisting of octreotide, sildenafil citrate, calcitriol, dihydrotachysterol, apomorphine, yohimbine, trazadone, acyclovir, cidofovir, delavirdine-mesylate, didanosine, famciclovir, foscarnet sodium, fluorouracil, ganciclovir sodium, idoxuridine, interferon-α, β, γ, lamivudine, nevirapine, penciclovir, ribavirin, stavudine, triflundine, valacyclovir-HCl, zalcitabine, zidovudine, indinavir-$H_2SO_4$, ritonavir, nelfinavir-$CH_3SO_3H$, saquinavir-$CH_3SO_3H$, d-penicillamine, chloroquine, hydroxychloroquine, aurothioglucose, gold sodium thiomalate, auranofin levamisole, dacarbazine, isoprinosine, methyl inosine monophosphate, muramyl dipeptide, diazoxide, hydralazine-HCl, and minoxidil.

19. The method of claim 8 wherein the pharmaceutical compound is selected from the group consisting of dipyridamole, isoxsuprine HCl, niacin, nylidrin-HCl, phentolamine, doxazosin-$CH_3SO_3H$, prazosin-HCl, terazocin-HCl, clonidine-HCl, nifedipine, molsidomine, amiodarone, acetylsalicylic acid, verapamil, diltiazem, nisoldipine, isradipine, bepridil, isosorbide-dinitrate, pentaerythrytol-tetranitrate, nitroglycerin, cimetidine, famotidine, nizatidine, ranitidine, lansoprazole, omeprazole, misoprostol, sucralfate, metoclopramide-HCl, erythromycin, alprostadil, albuterol, pirbuterol, terbutaline-$H_2SO_4$, salmetrol, aminophylline, dyphylline, ephedrine, ethylnorepinephrine, isoetharine, isoproterenol, metaproterenol, nedocromil, oxtriphylline, theophylline, bitolterol, fenoterol, budesonide, flunisolide, beclomethasone-dipropionate, fluticasone-propionate, codeine, codeine sulfate, and codeine phosphate.

20. The method of claim 8 wherein the pharmaceutical compound is selected from the group consisting of dextromethorphan HBr, triamcinolone-acetonide, montelukast sodium, zafirlukast, zileution, cromolyn sodium, ipratropium bromide, nedocromil sodium benzonate, diphenhydramine-HCl, hydrocodone-bitartarate, methadone-HCl, morphine sulfate, acetylcysteine, guaifenesin, ammonium carbonate, ammonium chloride, antimony potassium tartarate, glycerin, terpin-hydrate, colfosceril palmitate, atorvastatin-calcium, cervastatin-sodium, fluvastatin-sodium, lovastatin, pravastatin-sodium, simvastatin, picrorrhiza kurroa, andrographis paniculata, moringa oleifera, albizzia lebeck, adhatoda vasica, curcuma longa, momordica charantia, gymnema sylvestre, terminalia arjuna, azadirachta indica, tinosporia cordifolia, metronidazole, amphotericin B, clotrimazole, fluconazole, haloprogin, and ketoconazole.

21. The method of claim 8 wherein the pharmaceutical compound is selected from the group consisting of griseofulvin, itraconazole, terbinafin-HCl, econazole-$HNO_3$, miconazole, nystatin, oxiconazole-$HNO_3$, sulconazole-$HNO_3$, cetirizine-2HCl, dexamethasone, hydrocortisone, prednisolone, cortisone, catechin and its derivatives, glycyrrhizin, glycyrrhizic acid, betamethasone, fludrocortisone acetate, flunisolide, fluticasone-propionate, methyl prednisolone, somastostatin, lispro, glucagon, acarbose, chlorpropamide, glipizide, glyburide, metformin-HCl, repaglinide, tolbutamide, colchicine, sulfinpyrazone, allopurinol, piroxicam, tolmetin sodium, indomethacin, ibuprofen, diflunisal, mefenamic acid, naproxen, trientine, sulindac, sulindac sulfone, selenium compounds insuline, heparin, ampicillin, amantadine, rimantadine, proinsulin, celecoxib, budesonide, salicylic acid and its derivatives.

22. The method of claim 17 wherein the pharmaceutical compound is selected from the group consisting of dipyridamole, isoxsuprine HCl, niacin, nylidrin-HCl, phentolamine, doxazosin-$CH_3SO_3H$, prazosin-HCl, terazocin-HCl, clonidine-HCl, nifedipine, molsidomine, amiodarone, acetylsalicylic acid, verapamil, diltiazem, nisoldipine, isradipine, bepridil, isosorbide-dinitrate, pentaerythrytol-tetranitrate nitroglycerin, cimetidine, famotidine, nizatidine, ranitidine, lansoprazole, omeprazole, misoprostol, sucralfate, metoclopramide-HCl, erythromycin, alprostadil, albuterol, pirbuterol, terbutaline-$H_2SO_4$, salmetrol, aminophylline, dyphylline, ephedrine, ethylnorepinephrine, isoetharine, isoproterenol, metaproterenol, nedocromil, oxtriphylline, theophylline, bitolterol, fenoterol, budesonide, flunisolide, beclomethasone-dipropionate, fluticasone-propionate, codeine, codeine sulfate, and codeine phosphate.

23. The method of claim 17 wherein the pharmaceutical compound is selected from the group consisting of dextromethorphan HBr, triamcinolone-acetonide, montelukast sodium, zafirlukast, zileution, cromolyn sodium, ipratropium bromide, nedocromil sodium benzonate, diphenhydramine-HCl, hydrocodone-bitartarate, methadone-HCl, morphine sulfate, acetylcysteine, guaifenesin, ammonium carbonate, ammonium chloride, antimony potassium tartarate, glycerin, terpin-hydrate, colfosceril palmitate, atorvastatin-calcium, cervastatin-sodium, fluvastatin-sodium, lovastatin, pravastatin-sodium, simvastatin, picrorrhiza kurroa, andrographis paniculata, moringa oleifera, albizzia lebeck, adhatoda vasica, curcuma longa, momordica charantia, gymnema sylvestre, terminalia arjuna, azadirachta indica, tinosporia cordifolia, metronidazole, amphotericin B, clotrimazole, fluconazole, haloprogin, and ketoconazole.

24. The method of claim 17 wherein the pharmaceutical compound is selected from the group consisting of griseofulvin, itraconazole, terbinafin-HCl, econazole-$HNO_3$, miconazole, nystatin, oxiconazole-$HNO_3$, sulconazole-$HNO_3$, cetirizine-2HCl, dexamethasone, hydrocortisone, prednisolone, cortisone, catechin and its derivatives, glycyrrhizin, glycyrrhizic acid, betamethasone, fludrocortisone acetate, flunisolide, fluticasone-propionate, methyl prednisolone, somastostatin, lispro, glucagon, acarbose, chlorpropamide, glipizide, glyburide, metformin-HCl, repaglinide, tolbutamide, colchicine, sulfinpyrazone, allopurinol, piroxicam, tolmetin sodium, indomethacin, ibuprofen, diflunisal, mefenamic acid, naproxen, trientine, sulindac, sulindac sulfone, selenium compounds insuline, heparin, ampicillin, amantadine, rimantadine, proinsulin, celecoxib, budesonide, salicylic acid and its derivatives.

* * * * *